US008827946B2

(12) United States Patent
Tsutsui et al.

(10) Patent No.: US 8,827,946 B2
(45) Date of Patent: Sep. 9, 2014

(54) INTRANASAL GRANISETRON AND NASAL APPLICATOR

(75) Inventors: Tatsuo Tsutsui, Yokohama (JP); Ryoichi Nagata, Kagoshima (JP); Shunji Haruta, Kagoshima (JP)

(73) Assignee: Shin Nippon Biomedical Laboratories, Ltd., Kagoshima-shi (JP)

( * ) Notice: Subject to any disclaimer, the term of this patent is extended or adjusted under 35 U.S.C. 154(b) by 43 days.

(21) Appl. No.: 12/848,850

(22) Filed: Aug. 2, 2010

(65) Prior Publication Data

US 2011/0045088 A1 Feb. 24, 2011

Related U.S. Application Data

(60) Provisional application No. 61/230,637, filed on Jul. 31, 2009, provisional application No. 61/260,367, filed on Nov. 11, 2009, provisional application No. 61/261,292, filed on Nov. 13, 2009.

(51) Int. Cl.

| | |
|---|---|
| ***A61M 13/00*** | (2006.01) |
| ***A61K 9/00*** | (2006.01) |
| ***A61M 15/00*** | (2006.01) |
| ***A61M 15/08*** | (2006.01) |
| ***A61K 31/435*** | (2006.01) |

(52) U.S. Cl.

CPC ............ *A61K 9/0043* (2013.01); *A61M 15/003* (2014.02); *A61M 15/08* (2013.01); *A61M 2205/075* (2013.01); *A61M 15/004* (2014.02); *A61K 31/435* (2013.01); *A61M 15/0038* (2014.02); *A61M 15/0028* (2013.01); *A61M 2202/064* (2013.01)

USPC ............. 604/58; 604/212; 604/215; 604/275; 604/514

(58) Field of Classification Search

USPC ........... 604/58, 212, 213, 215, 217, 275, 514; 128/200.21–200.23, 203.15, 203.28, 128/207.18

See application file for complete search history.

(56) References Cited

U.S. PATENT DOCUMENTS

| | | | | |
|---|---|---|---|---|
| 3,906,950 A | | 9/1975 | Cocozza | |
| 4,013,075 A | * | 3/1977 | Cocozza | 128/203.15 |
| 4,159,345 A | | 6/1979 | Takeo et al. | |
| 4,226,233 A | | 10/1980 | Kritzer | |

(Continued)

FOREIGN PATENT DOCUMENTS

| | | |
|---|---|---|
| EP | 0122036 A1 | 10/1984 |
| EP | 0147755 A2 | 7/1985 |

(Continued)

OTHER PUBLICATIONS

"Fluorouracil" definition viewed on the National Cancer Institute website at www.cancergov/drugdictionary?cdrid=43130 on May 31, 2012.

(Continued)

*Primary Examiner* — Emily Schmidt

(74) *Attorney, Agent, or Firm* — Wilson Sonsini Goodrich & Rosati, PC

(57) ABSTRACT

Formulations and methods of manufacture are provided for granisetron dry powder compositions suitable for intranasal administration. Also provided are methods of use for preventing or controlling emesis and other diseases and disorders and devices, compositions, and methods for nasal delivery of therapeutic formulations. Devices for delivery of dry powder formulations are also provided. Devices can be single-use devices.

48 Claims, 9 Drawing Sheets

(56) References Cited

U.S. PATENT DOCUMENTS

| | | | | |
|---|---|---|---|---|
| 4,300,545 | A * | 11/1981 | Goodnow et al. | 128/200.14 |
| 4,613,500 | A | 9/1986 | Suzuki et al. | |
| 4,889,114 | A | 12/1989 | Kladders | |
| 5,098,907 | A | 3/1992 | Kondo et al. | |
| 5,320,094 | A | 6/1994 | Laube et al. | |
| 5,419,315 | A * | 5/1995 | Rubsamen | 128/200.14 |
| 5,647,349 | A | 7/1997 | Ohki et al. | |
| 5,672,581 | A | 9/1997 | Rubsamen et al. | |
| 5,674,507 | A | 10/1997 | Banker et al. | |
| 5,683,361 | A | 11/1997 | Elk et al. | |
| 5,731,303 | A | 3/1998 | Hsieh | |
| 5,756,483 | A | 5/1998 | Merkus et al. | |
| 5,804,209 | A | 9/1998 | De Ponti et al. | |
| 5,810,004 | A | 9/1998 | Ohki et al. | |
| 5,939,100 | A | 8/1999 | Albrechtsen et al. | |
| 5,942,242 | A | 8/1999 | Mizushima et al. | |
| 5,948,749 | A | 9/1999 | Igarashi et al. | |
| 5,958,458 | A | 9/1999 | Norling et al. | |
| 5,989,217 | A * | 11/1999 | Ohki et al. | 604/94.01 |
| 6,136,295 | A | 10/2000 | Edwards et al. | |
| 6,197,328 | B1 | 3/2001 | Yanagawa | |
| 6,248,363 | B1 | 6/2001 | Patel et al. | |
| 6,273,086 | B1 | 8/2001 | Ohki et al. | |
| 6,298,846 | B1 | 10/2001 | Ohki et al. | |
| 6,516,795 | B1 | 2/2003 | Bougamont et al. | |
| 6,815,424 | B2 | 11/2004 | Vickery et al. | |
| 6,824,080 | B2 | 11/2004 | Matsugi et al. | |
| 6,835,389 | B1 | 12/2004 | Dohi et al. | |
| 6,855,913 | B2 | 2/2005 | Nikodym | |
| 6,906,027 | B2 | 6/2005 | Oki et al. | |
| 7,115,281 | B2 | 10/2006 | Singh et al. | |
| 7,278,982 | B2 | 10/2007 | Tsutsui | |
| 7,306,787 | B2 | 12/2007 | Tarara et al. | |
| 7,353,823 | B2 | 4/2008 | Tsutsui | |
| 7,638,138 | B2 | 12/2009 | Oki et al. | |
| 7,806,117 | B2 | 10/2010 | Tsutsui | |
| 2001/0027301 | A1* | 10/2001 | Lau et al. | 604/310 |
| 2001/0038824 | A1 | 11/2001 | Horii et al. | |
| 2002/0002172 | A1 | 1/2002 | Bell-huff et al. | |
| 2002/0012688 | A1 | 1/2002 | Dohi et al. | |
| 2002/0040139 | A1 | 4/2002 | Billotte et al. | |
| 2002/0062829 | A1 | 5/2002 | Ohki et al. | |
| 2003/0199424 | A1 | 10/2003 | Smith et al. | |
| 2004/0063615 | A1 | 4/2004 | Oki et al. | |
| 2004/0076588 | A1 | 4/2004 | Batycky et al. | |
| 2004/0092428 | A1 | 5/2004 | Chen et al. | |
| 2004/0173211 | A1 | 9/2004 | Kladders et al. | |
| 2004/0241232 | A1 | 12/2004 | Brown et al. | |
| 2005/0022812 | A1* | 2/2005 | Hrkach | 128/203.15 |
| 2005/0042177 | A1 | 2/2005 | Ryde et al. | |
| 2005/0142073 | A1 | 6/2005 | Watts et al. | |
| 2005/0177095 | A1 | 8/2005 | Tsutsui | |
| 2006/0106057 | A1 | 5/2006 | Daniel et al. | |
| 2006/0116657 | A1* | 6/2006 | Schmid | 604/416 |
| 2006/0216352 | A1 | 9/2006 | Nystrom et al. | |
| 2006/0217658 | A1 | 9/2006 | Tsutsui | |
| 2006/0233715 | A1 | 10/2006 | Oki et al. | |
| 2007/0055200 | A1* | 3/2007 | Gilbert | 604/70 |
| 2007/0060509 | A1 | 3/2007 | Kanikanti et al. | |
| 2007/0060868 | A1 | 3/2007 | Tsutsui | |
| 2007/0098804 | A1 | 5/2007 | Aronhime et al. | |
| 2007/0178164 | A1 | 8/2007 | Blau | |
| 2007/0184109 | A1 | 8/2007 | Floyd et al. | |
| 2007/0249674 | A1 | 10/2007 | Bolton et al. | |
| 2007/0272763 | A1* | 11/2007 | Dunne et al. | 239/8 |
| 2008/0029084 | A1 | 2/2008 | Costantino et al. | |
| 2008/0031959 | A1 | 2/2008 | Blondino et al. | |
| 2008/0090841 | A1 | 4/2008 | Johnson et al. | |
| 2008/0127972 | A1 | 6/2008 | Morton | |
| 2008/0260848 | A1 | 10/2008 | Nagata et al. | |
| 2008/0286362 | A1 | 11/2008 | Baran Jr. et al. | |
| 2009/0157037 | A1* | 6/2009 | Iyer et al. | 604/403 |
| 2009/0169640 | A1 | 7/2009 | Oki et al. | |
| 2010/0178331 | A1 | 7/2010 | Nagata et al. | |
| 2011/0033544 | A1 | 2/2011 | Nagata et al. | |
| 2013/0287852 | A1 | 10/2013 | Oki et al. | |

FOREIGN PATENT DOCUMENTS

| | | | |
|---|---|---|---|
| EP | 0761248 | A1 | 3/1997 |
| EP | 0943326 | A1 | 9/1999 |
| EP | 1025859 | A1 | 8/2000 |
| EP | 1108423 | A1 | 6/2001 |
| EP | 1454648 | A1 | 9/2004 |
| EP | 1504780 | A1 | 2/2005 |
| EP | 1785145 | A1 | 5/2007 |
| GB | 2395900 | A | 6/2004 |
| JP | 3912469 | | 7/1964 |
| JP | 53127553 | | 11/1978 |
| JP | 54062328 | | 5/1979 |
| JP | 59-34267 | A | 2/1984 |
| JP | S 59-163313 | A | 9/1984 |
| JP | 60-185564 | | 9/1985 |
| JP | 60-224616 | | 11/1985 |
| JP | 62-42888 | | 9/1987 |
| JP | 63267731 | | 11/1988 |
| JP | 3-29146 | | 3/1991 |
| JP | 5-32560 | | 2/1993 |
| JP | 7-165613 | A | 6/1995 |
| JP | 8-098888 | | 4/1996 |
| JP | H 08-206208 | A | 8/1996 |
| JP | 08243164 | | 9/1996 |
| JP | 9-276405 | | 10/1997 |
| JP | 9-291026 | A | 11/1997 |
| JP | 10-59841 | A | 3/1998 |
| JP | 10059841 | | 3/1998 |
| JP | 11/216357 | | 8/1999 |
| JP | 11-322582 | | 11/1999 |
| JP | 2000-229859 | A | 8/2000 |
| JP | 2000-239187 | | 9/2000 |
| JP | 2001-55323 | A | 2/2001 |
| JP | 2002-255795 | A | 9/2002 |
| JP | 2003-154006 | A | 5/2003 |
| JP | 2003-175103 | A | 6/2003 |
| JP | 2003-206227 | A | 7/2003 |
| WO | WO 94/04133 | A1 | 3/1994 |
| WO | WO 95/12399 | A1 | 5/1995 |
| WO | WO 95/34582 | A1 | 12/1995 |
| WO | WO 97/31626 | A1 | 9/1997 |
| WO | WO 98/30207 | A1 | 7/1998 |
| WO | WO 99/16422 | A1 | 4/1999 |
| WO | WO 99/16470 | A1 | 4/1999 |
| WO | WO 99/51205 | A1 | 10/1999 |
| WO | WO 00/12063 | A1 | 3/2000 |
| WO | WO 00/12136 | A1 | 3/2000 |
| WO | WO 00/23023 | A1 | 4/2000 |
| WO | WO 00/38811 | A1 | 7/2000 |
| WO | WO 01/26630 | A1 | 4/2001 |
| WO | WO 01/32125 | A2 | 5/2001 |
| WO | WO 02/32406 | A2 | 4/2002 |
| WO | WO 02/094233 | A1 | 11/2002 |
| WO | WO 03/004048 | A1 | 1/2003 |
| WO | WO 03/030872 | A2 | 4/2003 |
| WO | WO 03/077825 | A2 | 9/2003 |
| WO | WO 03/095008 | A1 | 11/2003 |
| WO | WO 2004/004922 | A1 | 1/2004 |
| WO | WO 2004/073729 | A1 | 9/2004 |
| WO | WO 2005/013937 | A2 | 2/2005 |
| WO | WO 2005/056008 | A1 | 6/2005 |
| WO | WO 2005/104712 | A2 | 11/2005 |
| WO | WO 2006/016530 | A1 | 2/2006 |
| WO | WO 2006/040680 | A1 | 4/2006 |
| WO | WO 2008/031028 | A2 | 3/2008 |
| WO | WO 2008/075102 | A1 | 6/2008 |
| WO | WO 2008/078730 | A1 | 7/2008 |
| WO | WO 2008/031028 | A3 | 11/2008 |
| WO | WO 2009/095684 | A1 | 8/2009 |

OTHER PUBLICATIONS

Hens, et al., "BMP4 and PTHrP interact to stimulate ductal outgrowth during embryonic mammary development and to inhibit hair follicle induction," Development 2007, 234, pp. 1221-1230.

(56) References Cited

OTHER PUBLICATIONS

Merriam-Webster's Collegiate Dictionary, 10th edition, Merriam-Webster Incorporated: Springfield, Massachusetts, 1993, pp. 41.
UK office action dated Apr. 10, 2012 for Application No. GB1012959.1.
European search report and opinion dated Dec. 19, 2011 for Application No. 07860016.0.
Office action dated Sep. 28, 2011 for JP Application No. 2006-531575 (in Japanese with English translation).
UK search report dated Sep. 9, 2011 for Application No. GB1012959.1.
European search report dated Jul. 15, 2008 for Application No. 05768543.0.
International search report dated May 7, 2003 for PCT Application No. JP2003/001948.
International search report dated Nov. 1, 2005 for PCT Application No. JP2005/014389.
International search report dated Feb. 5, 2008 for PCT Application No. JP2007/074787.
International search report Jun. 8, 2010 for PCT Application No. JP2010/003285.
Kleinebudde, et al. Influence of degree of polymerization on behavior of cellulose during homogenization and extrusion/spheronization. AAPS Pharmasci 2000, 2(2) Article 21, 1-10.
Rowe, et al (Eds). Handbook of Pharmaceutical Excipients. Pharmaceutical Press. 2003. p. 108-109.
UK combined office action and search report dated Nov. 10, 2010 for Application No. GB1012959.1.
International search report (partial) dated Dec. 21, 2010 for PCT Application No. IB2010/02168.
U.S. Appl. No. 12/576,219, filed Oct. 8, 2009, Tsutsui et al.
International search report and written opinion dated Jun. 28, 2011 for PCT Application No. IB2010/02168.
U.S. Appl. No. 13/649,515, filed Oct. 11, 2012, Nagata et al.
Office action dated Jan. 6, 2014 for U.S. Appl. No. 12/576,219.
Component definition, Dictionary.com, accessed Apr. 1, 2014, pp. 1-4.
Labiris, et al. Pulmonary drug delivery. Part I: physiological factors affecting therapeutic effectiveness of aerosolized medications. Br J Clin Pharmacol. Dec. 2003;56(6):588-99.
Office action dated Apr. 8, 2014 for U.S. Appl. No. 13/827,859.
Office action dated Apr. 9, 2014 for U.S. Appl. No. 12/780,433.
Partition Coefficient, Wikipedia, accessed Mar. 31, 2014, pp. 1-8.
Topliss, John. Quantitative Structure-Activity Relationships of Drugs, 1983, pp. 2.
European search report and opinion mailed Dec. 20, 2013 for Application No. 10774745.3.
Hibberd, et al. Immunization strategies for the immunocompromised host: the need for immunoadjuvants. Ann Intern Med. 1989 Jun 15;110(12):955-6.
Ishikawa, et al. Improved nasal bioavailability of elcatonin by insoluble powder formulation. Int J Pharm. Aug. 14, 2001;224(1-2):105-14.
Office action dated Jan. 13, 2011 for U.S. Appl. No. 12/346,537.
Office action dated Jan. 20, 2011 for U.S. Appl. No. 12/576,219.
Office action dated Jan. 29, 2008 for U.S. Appl. No. 10/545,764.
Office action dated Apr. 12, 2012 for U.S. Appl. No. 12/576,219.
Office action dated Apr. 20, 2012 for U.S. Appl. No. 12/780,433.
Office action dated May 7, 2013 for U.S. Appl. No. 11/660,131.
Office action dated Jun. 4, 2012 for U.S. Appl. No. 12/521,116.
Office action dated Jun. 10, 2013 for U.S. Appl. No. 12/576,219.
Office action dated Jun. 25, 2012 for U.S. Appl. No. 12/346,537.
Office action dated Sep. 6, 2011 for U.S. Appl. No. 12/346,537.
Office action dated Sep. 6, 2011 for U.S. Appl. No. 12/576,219.
Office action dated Sep. 20, 2013 for U.S. Appl. No. 13/827,859.
Office action dated Sep. 24, 2008 for U.S. Appl. No. 10/545,764.
Office action dated Sep. 27, 2010 for U.S. Appl. No. 11/660,131.
Office action dated Oct. 10, 2012 for U.S. Appl. No. 12/780,433.
Office action dated Oct. 29, 2009 for U.S. Appl. No. 11/660,131.
Office action dated Nov. 1, 2012 for U.S. Appl. No. 11/660,131.
Office action dated Dec. 5, 2011 for U.S. Appl. No. 12/346,537.

* cited by examiner

INTRANASAL GRANISETRON AND NASAL APPLICATOR

CROSS REFERENCES

This application claims the benefit of and priority to U.S. Provisional Application No. 61/230,637, filed Jul. 31, 2009; U.S. Provisional Application No. 61/260,367, filed Nov. 11, 2009; and U.S. Provisional Application No. 61/261,292, filed Nov. 13, 2009, which applications are incorporated herein by reference.

BACKGROUND OF THE INVENTION

Many cancer chemotherapies induce emesis in patients with some patients experiencing emesis in anticipation of receiving therapy. Oral anti-emetics suffering from slow onset of action are subject to first-pass metabolism. Intravenous (IV) dosing is invasive and is not suited for patient self-administration. A dry powder intranasal formulation was developed that provides for fast onset of action, high bioavailability, and ease of use allowing for self-administration.

Devices and methods for delivering a powdered therapeutic formulation into the nostril and/or nasal cavity of a subject (e.g. a patient) are generally known and include devices and methods described in U.S. Pat. Nos. 7,278,982, and 7,438,700 herein incorporated by reference in their entirety. Reusable devices must be regularly cleaned and maintained to prevent contamination, assure good hygiene and proper operation. Additionally, devices can fail to deliver a consistent or reproducible dose. In the case of devices comprising a capsule or other loadable external medicine container, there exists the logistical problem of assuring an adequate supply of both the nasal applicator and the consumable capsule or other loadable external medicine container. Capsules and other loadable external medicine containers further present the problem of loading a dose that can require a certain level of physical dexterity or additional training of the user to ensure proper loading. Also, the prior art devices do not provide an easily or convenient way for determining the amount of therapeutic actually delivered to the subject or to check if there is residual powdery formulation in a device. Additionally, size and weight of many of devices impose a burden on the user to carry a device about or prove awkward to hold or use. Methods and compositions described herein address these and other issues thereby providing a simple and more convenient way for a patient or caregiver to be able to intranasally administer a therapeutic agent.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE INVENTION

Provided herein are improved devices and methods that can effectively overcome the drawbacks encountered in conventional nasal delivery devices. Additionally, the present disclosure provides unit dosages of dry powder granisetron, kits containing such unit dosages, and systems for intranasal administration of the dry powder formulations provided herein. Methods of preventing and/or treating emesis using the dry powder formulations, kits and systems are also provided.

Disclosed herein are devices comprising a nozzle having an upstream end and a downstream end adapted to allow positioning of at least a portion of said nozzle into a nostril of a subject; a reservoir comprising a single dose of a powdered therapeutic formulation, a reservoir having an upstream end and a downstream end, and disposed within said nozzle; a valve assembly having an upstream end and a downstream end, wherein the downstream end is coupled to the upstream end of a reservoir; and an air source operably linked to the upstream end of a valve assembly; wherein a device is a single-use device. In some embodiments, a device is adapted to deliver between 80% and 99% of the single dose of powdered therapeutic formulation into the nostril of the subject. In other embodiments, a device is adapted to deliver between 80% and 99% of the single dose of powdered therapeutic formulation into the nostril of the subject after a single activation of an air source. In further embodiments, an air source is adapted to deliver between 2 and 7 mL of air. In other embodiments, a device is adapted to deliver between 1 and 50 mg of powdered therapeutic agent. In some embodiments, a device is less than 50 $cm^3$ in volume, while in other embodiments a device has a mass of less than 20 grams.

An air source can be adapted to be engaged by a user to force air from an air source through a valve assembly into a reservoir and out the downstream end of the nozzle. A device can also be adapted to provide a laminar airflow within at least a portion of a reservoir while a device is in use. In some embodiments, an air source comprises a pump. A device can be adapted to deliver a powdered therapeutic composition into the nostril of the subject by application of between about 5 and about 30 kilopascals of compressive force to a pump. A pump can comprise a deformable volume adapted to be engaged by a user. A valve assembly useful in embodiments disclosed herein can further comprise a rigid backing disposed over at least a portion of a pump. In some embodiments, a pump comprises a manual air pump. A manual air pump can be adapted to be engaged by a user by squeezing a pump between a thumb and a forefinger, middle finger, ring finger, little finger or combination thereof.

A reservoir of a device disclosed herein can comprise an inner diameter of less than 10 mm. A downstream end of a reservoir can comprise a flow restrictor. In some embodiments, the nozzle of a device comprises a length perpendicular to an upstream to downstream axis of between 5 mm and 20 mm or comprises a length parallel to an upstream to downstream axis of between 5 mm and 40 mm. A nozzle in some devices disclosed herein can comprise an airtight cap positioned on the upstream end of the nozzle and adapted to prevent outside air from contacting a powdered therapeutic formulation. In other embodiments, the nozzle comprises a breakable cover positioned at the downstream end of the nozzle, and adapted to prevent a flow of air through the nozzle. In some embodiments, the nozzle is tapered and comprises a funnel shape with an upstream end and a downstream end wherein the downstream end of the flow restrictor is narrower than the upstream end.

In some embodiments, an air source comprises a flow inlet that is less than 10% of the size of a flow outlet of a valve assembly. In further embodiments, a flow inlet is between 0.1 and 2 mm in diameter.

In some embodiments, a valve assembly of a device comprises a diffuser with an upstream end and a downstream end, wherein the downstream end of a diffuser is operably linked to the upstream end of a reservoir. In other embodiments, a diffuser comprises a funnel shape with an upstream end and a downstream end wherein the upstream end of a diffuser is narrower than the downstream end. In some embodiments, a valve assembly comprises a throat with an upstream end and a downstream end, wherein the downstream end of a throat is operably linked to the upstream end of a diffuser. In some embodiments, a valve assembly further comprises a check valve adapted to regulate a flow of air. In some embodiments, a valve assembly comprises a poppet. In other embodiments, a poppet is adapted to provide laminar airflow along at least a portion of a reservoir. In further embodiments, a poppet is adapted to block the movement of a powdered therapeutic formulation into a valve assembly. In other embodiments, a valve assembly comprises a poppet, at least a portion of which is disposed within a throat.

In some embodiments, a valve assembly of a device comprises a check valve that is attached to a poppet that comprises of a downstream deflecting surface and an upstream stem. A deflecting surface is adapted to direct a flow of air along at least a portion of a reservoir, and a stem is operably linked to a check valve. In some embodiments, a check valve comprises a valve disk adapted to move from a first position and a second position, a valve disk comprising an upstream surface adapted to regulate the flow of air from an air source through a flow outlet and into a reservoir, wherein in the first position the upstream surface is in communication with a flow outlet and thereby the flow of air into a reservoir is blocked, and in the second position the flow of air into reservoir is allowed. In some embodiments, a check valve comprises a valve disk adapted to move from a first position and a second position. In further embodiments, a valve disk comprises of an upstream surface adapted to regulate the flow of air from an air source through a flow outlet and into a reservoir, wherein in the first position the upstream surface is in communication with a flow outlet and the flow of air into a reservoir is blocked, and in the second position the flow of air into a reservoir is allowed; and a downstream surface operably linked to the stem of a poppet, wherein the movement of a valve disk from the first position to the second position moves a poppet from a first position to a second position, and wherein in the first position a poppet is adapted to block upstream movement of a powdered therapeutic formulation, and in the second position a poppet is adapted to direct the flow of air along at least a portion of a reservoir.

In some embodiments, a check valve further comprises a spring operable to maintain a valve disk in the first position absent a sufficient flow of air, and wherein a spring is operable to maintain a valve disk in the second position in the presence of the sufficient flow of air. In some embodiments, sufficient flow of air is generated by a compression force of at least 20 kilopascals applied to an air source. In some embodiments, a deflecting surface of a poppet in the second position is disposed within a diffuser of a valve assembly.

In some embodiments, the nozzle is comprised of a substantially clear or translucent material. In other embodiments, the nozzle comprises of at least one engaging ratchet adaptable to secure the nozzle to a valve assembly. In some embodiments, the nozzle further comprises an engaging hole adaptable to secure the nozzle to a valve assembly. In some embodiments, a valve assembly comprises of at least one engaging hole adaptable to secure a valve assembly to the nozzle. In other embodiments, a valve assembly comprises of at least one engaging ratchet adaptable to secure a valve assembly to the nozzle.

In one aspect, a method is provided for using a device to deliver a powdered therapeutic formulation, wherein a device is a single-use device that comprises of a nozzle having an upstream end and a downstream end, said nozzle adapted to allow positioning of at least a portion of said nozzle into a nostril of a subject; a reservoir comprising a dose of a powdered therapeutic formulation and having an upstream end and a downstream end, operably linked to and disposed within said nozzle; a valve assembly having an upstream end and a downstream end, wherein the downstream end is coupled to the upstream end of a reservoir; and a manual air pump operably linked to the upstream end of a valve assembly. The method for using a device comprises of positioning the nozzle of a device into the nostril of the subject and activating a pump. In some embodiments, the nozzle and reservoir of a device comprises clear or translucent material and the user visually inspects the amount of powdered therapeutic formulation remaining in a reservoir at a first activation. If there is remaining material in a reservoir, the user repeats the method of administration until a sufficient dose is delivered as exemplified by little or no powdery therapeutic formulation remaining in a reservoir. In some embodiments, the method delivers between about 80% to about 99% of the single dose of powdered therapeutic formulation to the user. In some embodiments, the method delivers between 1 mg and 50 mg of a powdered therapeutic formulation to the user.

In some embodiments, the administration method comprises activating the manual air pump to produce laminar flow along at least a portion of a reservoir. In further embodiments, the manual air pump is compressed with between 5 and 30 kilopascals of force.

In one aspect, a method is provided for manufacturing a device for delivering a powdered therapeutic formulation to a subject, wherein a device comprises of a nozzle having an upstream end and a downstream end, said nozzle adapted to allow positioning of at least a portion of said nozzle into a nostril of a subject; a reservoir comprising a dose of a powdered therapeutic formulation and having an upstream end and a downstream end, operably linked to and disposed within said nozzle; a valve assembly having an upstream end and a downstream end, wherein the downstream end is coupled to the upstream end of a reservoir; and a manual air pump operably linked to the upstream end of a valve assembly. The manufacturing method comprises of providing a powdered therapeutic formulation to a reservoir and subsequently coupling the nozzle to a valve assembly.

Provided herein are unit dosages of a dry powder granisetron formulation suitable for intranasal administration, wherein when administered as a prophylaxis to cancer patients prior to administration of cancer chemotherapy, emesis is prevented in at least 80% of the patients. In one embodiment, the emesis is prevented is in at least 90% of the patients. In another embodiment, a formulation is encapsulated. In another embodiment, hydroxyproplyl methylcellulose is the encapsulating material of a formulation. In another embodiment, a formulation comprises from about 0.5 mg to about 16 mg of granisetron, when measured as the freebase. In another embodiment, a median $C_{max}$ of at least 4 ng/mL is observed in the use of a formulation. In another embodiment, a median $C_{max}$ of at least 10 ng/mL is observed in the use of a formulation. In another embodiment, a median $C_{max}$ of at least 20 ng/mL is observed in the use of formulation. In another embodiment, a median $T_{max}$ of less than 0.8 hours is observed in the use of formulation. In another embodiment, a median $T_{max}$ of less than 0.6 hours is observed in the use of formulation. In another embodiment, a median $T_{1/2}$ of between 8-10 hours is observed in the use of formulation. In another embodiment, a formulation has an absolute bioavailability is at least 90%. In another embodiment, a formulation has an absolute bioavailability is at least 95%. In another embodiment, the cancer chemotherapy is highly emetogenic. In another embodiment, the highly emetogenic chemotherapy is selected from cisplatin, mechlorethamine, streptozcin, cyclophosphamide, carmustine, dacarbazine, hexamethylmelamine or procarbazine. In another embodiment, the emetogenic chemotherapy further comprises an additional cancer chemotherapy agent selected from carboplatin, cytarabine, doxorubicin, methotrexate, epirubicin, idarubicin, ifosfamide, or mitoxantrone. In another embodiment, 90% or more of the particles of a formulation are less than 300 μm in diameter. In another embodiment, 90% or more of the particles of a formulation are less than 150 μm in diameter. In another embodiment, 90% or more of the particles of a formulation are less than 100 μm in diameter. In another embodiment, 90% or more of the particles of a formulation are less than 65 μm in diameter. In another embodiment, at least 96% of granisetron is present after storage for 1 year at room temperature. In another embodiment, a unit dosage weighs about 50 mg or less. In another embodiment, the weight of granisetron, measured as the freebase, is about 16 mg or less. In another embodiment, granisetron is about 300 μm or less in diameter.

Provided herein are kits comprising a unit dosage of a dry powder granisetron formulation suitable for intranasal administration and a nasal applicator. In one embodiment, a unit dosage is a capsule. In another embodiment, the nasal applicator has a volume of about 50 mL or less. In another embodiment, a unit dosage comprises about 0.5 mg, 1.0 mg, 2.0 mg, 4.0 mg, 8.0 mg, 16.0 mg of granisetron or less.

Provided herein are systems comprising a unit dosage of a dry powder granisetron formulation suitable for intranasal administration and a nasal applicator the system delivers at least 80% of granisetron in a unit dosage to a patient. Such a system may comprise a unit dosage of a dry powder granisetron formulation suitable for intranasal administration and a nasal applicator, wherein when activated, the system produces a plume geometry wherein a plume is produced with an angle of less than 45 degrees when the plume is measured at a distance of 30 mm from a nozzle of the applicator.

Provided herein are methods of preventing or treating emesis comprising: administering to a patient in need thereof, an effective dose of granisetron is formulated as a dry powder and wherein the dry powder formulation is administered intranasally. In one embodiment, the patient will be or is currently undergoing treatment with at least one cancer chemotherapy agent. In another embodiment, the effective dose of granisetron prevents emesis in at least 80% of the patients. In another embodiment, the effective dose of granisetron prevents emesis in at least 90% of the patients. In another embodiment, the effective dose of granisetron controls breakthrough emesis in at least 80% of the patients. In another embodiment, the effective dose of granisetron is about 0.5 mg, 1.0 mg, 2.0 mg, 4.0 mg, 8 mg, or 16 mg when measured as a freebase. In another embodiment, the effective dose of granisetron is 16 mg or less, when measured as a freebase. In another embodiment, the effective dose of granisetron does not have an objectionable taste. In another embodiment, a $C_{max}$ of at least 4 ng/mL is achieved by the use of the system. In another embodiment, a $C_{max}$ of at least 10 ng/mL is achieved by the use of the system. In another embodiment, a $C_{max}$ of at least 20 ng/mL is achieved by the use of the system. In another embodiment, a $T_{max}$ of 0.8 hour or less is observed in the use of the system. In another embodiment, a $T_{max}$ of 0.6 hour or less is observed in the use of the system. In another embodiment, a $T_{1/2}$ of between 8 to 10 hours is observed in the use of the system. In another embodiment, a plasma level of 5 ng/mL of granisetron is achieved by the use of the system for at least 4 hours.

Provided herein is a pharmaceutical kit comprising at least one dosage unit of an inhalable dry powder formulation of granisetron and an applicator for nasal administration. In one embodiment, the at least one dosage unit is a capsule.

BRIEF DESCRIPTION OF THE DRAWINGS

The novel features are set forth with particularity in the appended claims. A better understanding of the features and advantages will be obtained by reference to the following detailed description that sets forth illustrative embodiments, in which the principles of devices, methods, and compositions are utilized, and the accompanying drawings of which:

DETAILED DESCRIPTION OF THE INVENTION

The present application provides dry powder formulations of pharmaceuticals for the treatment and/or prophylaxis of disorders, such as emesis following cancer therapy. Described herein are dry powder formulations, for example a dry powder formulation containing granisetron, with enhanced pharmacokinetic properties and/or enhanced deliverability. Kits and systems containing the dry powder formulations are further described. In some instances, an applicator device is used for dosing a person in need of treatment. Dosing can be performed by a medical professional and/or by the person in need of treatment (e.g., a patient). As described herein, devices can be pre-loaded with a dry powder formulation described herein, or a device can be constructed so as to receive a packaged dry powder formulation (e.g., a capsule containing the formulation which is pierced, broken, or otherwise ruptured so as to allow dispensing of the formulation by the device). In some instances, the device is a single-use device. A novel feature of the single-use devices disclosed herein is the presence of a poppet which allows for directed airflow to achieve a high rate of clearance of a composition from the devices.

I. Devices

Provided herein are nasal applicators comprising a nozzle, a valve assembly, and an air or gas source. The nozzle is in communication with the air or gas source through a valve assembly that can regulate the flow of air or gas into the nozzle.

Figure 1:
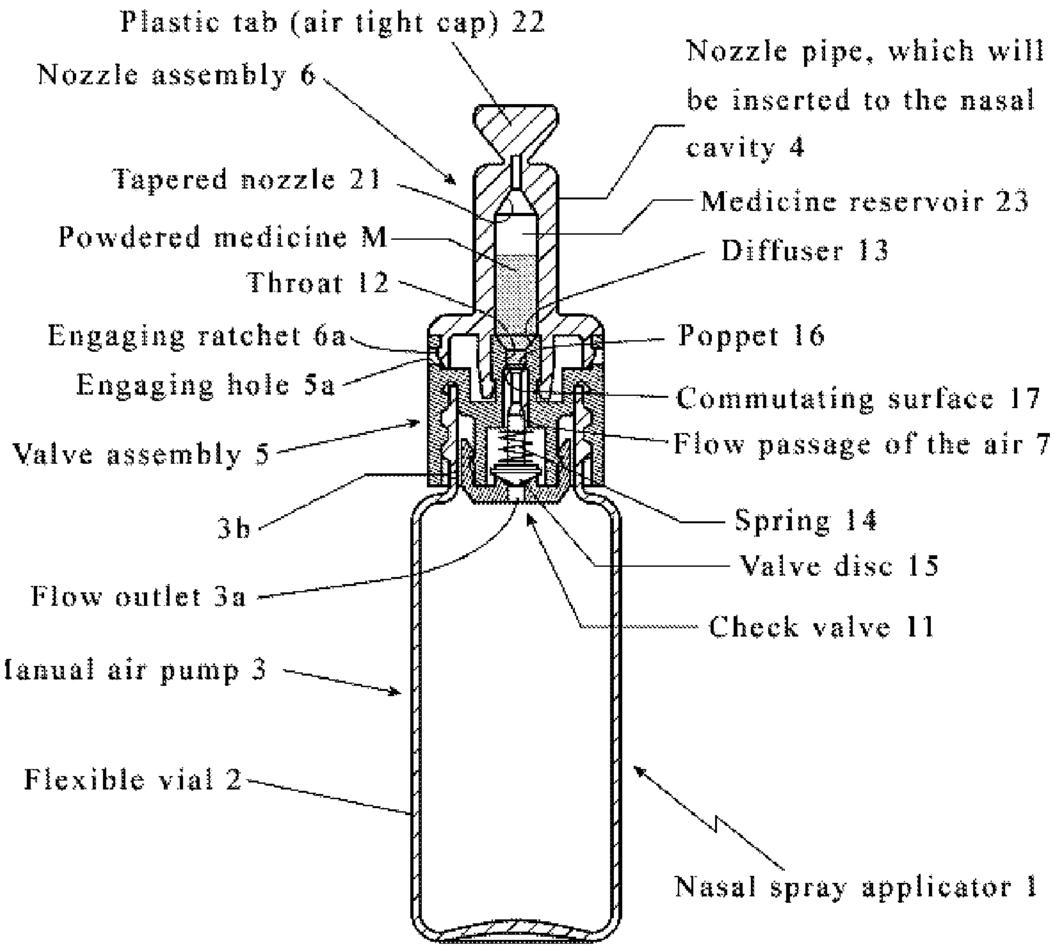
FIG. 1 illustrates a cross sectional view of a nasal spray applicator described herein.

Devices as described herein can be more fully understood by reference to the figures provided herein. FIG. 1 illustrates a single-use nasal spray applicator device. A device (1) is comprised of a deformable volume (2) and a flow inlet (3*b*) which comprises a manual air pump (3). A device (1) is further comprised of a valve assembly (5) which comprises a check valve (11) which comprises a flow outlet (3*a*), a valve disk (15), a spring (14), a flow passage (7), and a poppet (16) which further comprises a deflecting surface (17). A poppet (16) is disposed within a flow passage (7) and a throat (12) which is in communication with a diffuser (13). A valve assembly further comprises one or more engaging holes (5*a*) for attachment to a nozzle (6). A device is further comprised of a nozzle (6) which comprises a nozzle pipe (4) which is adapted to be inserted or partially inserted into the nasal cavity or a nostril of a subject. The nozzle (6) further comprises a flow restrictor (21), a breakable cover (22), and a powdered therapeutic reservoir (23). The powdered medicine reservoir comprises powdered therapeutic formulation (M). The nozzle (6) further comprises one or more ratchets (6*a*) for attachment to a valve assembly (5). The devices disclosed herein can be of any convenient dimensions for application of the therapeutic compositions contained therein, for example, a device could be between 1-6 inches in height, such as about 1 inch, about 1.5 inches, about 2 inches, about 2.5 inches, about 3 inches, about 3.5 inches, about 4 inches, about 4.5 inches, about 5 inches, about 5.5 inches, or about 6 inches in height. Dimensions for the device can be chosen based on the amount of therapeutic composition to be delivered, ease of use, ease of portability, or manufacturing convenience.

Figure 2:
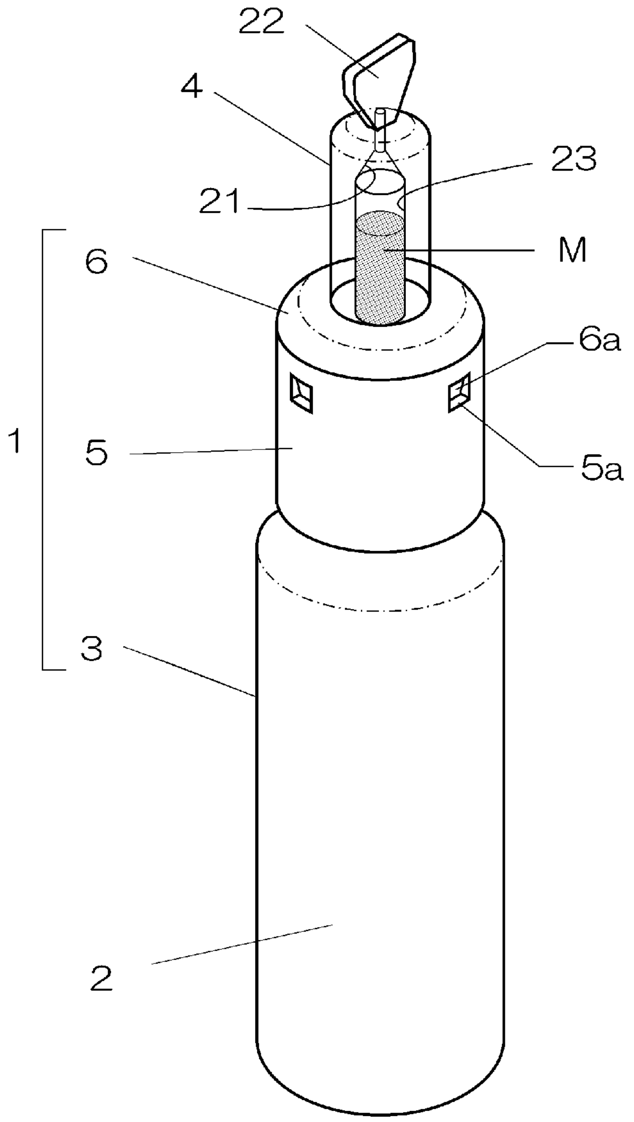
FIG. 2 illustrates an external view of a nasal spray applicator described herein.

FIG. 2 illustrates an external view of a nasal spray applicator device. A device (1) is comprised of a manual air pump (3) which comprises a deformable volume (2), a valve assembly (5), and a nozzle (6). A valve assembly further comprises a plurality of engaging holes (5*a*) which interact with the nozzle (6) through a plurality if ratchets (6*a*) for attachment of a valve assembly (5) to the nozzle (6). The nozzle (6) further comprises a powdered therapeutic formulation (M) disposed within a translucent reservoir (23), a translucent nozzle pipe (4), a flow restrictor (21), and a breakable cover (22).

Figure 3:
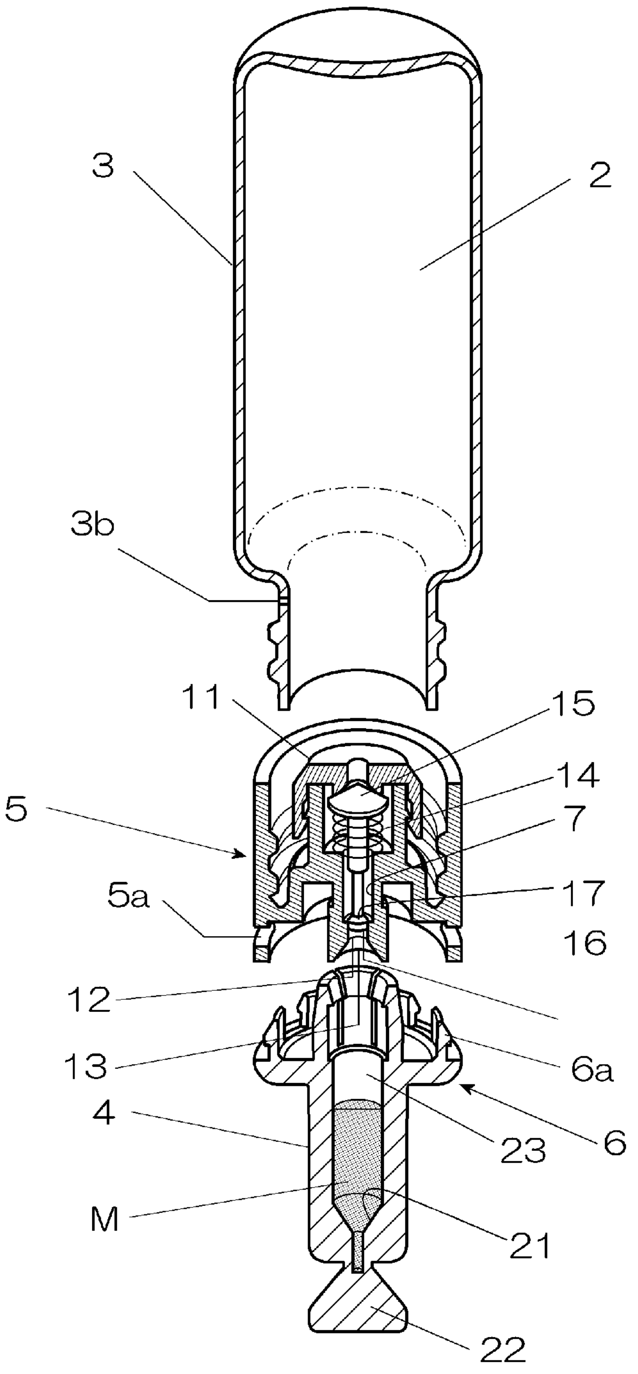
FIG. 3 illustrates an exploded view of a nasal spray applicator described herein.

FIG. 3 illustrates a method of manufacturing a nasal spray applicator device. A manual air pump (3) comprising a deformable volume (2) and a flow inlet (3*b*) can be manufactured as a single piece. A valve assembly (5) comprising a check valve (11), a valve disk (15), a spring (14), a flow passage (7), a poppet (16), a deflecting surface (17), a throat (12), a diffuser (13), and one or more engaging holes (5*a*) can be manufactured as a unit. A nozzle (6) comprising one or more ratchets (6*a*), a nozzle pipe (4), a powdered therapeutic formulation reservoir (23), a flow restrictor (21), and a breakable cover (22) can be manufactured as a unit. A powdered therapeutic formulation reservoir (23) can then be filled with a powdered therapeutic formulation (M). Finally, the nozzle (6) can be affixed to a valve assembly (5). A valve assembly can first be affixed to the manual air pump (3). A nozzle (6) can be affixed to a valve assembly (5) prior to attachment of the manual air pump (3) to a valve assembly (5). All three components can be attached at the same time.

Figure 4:
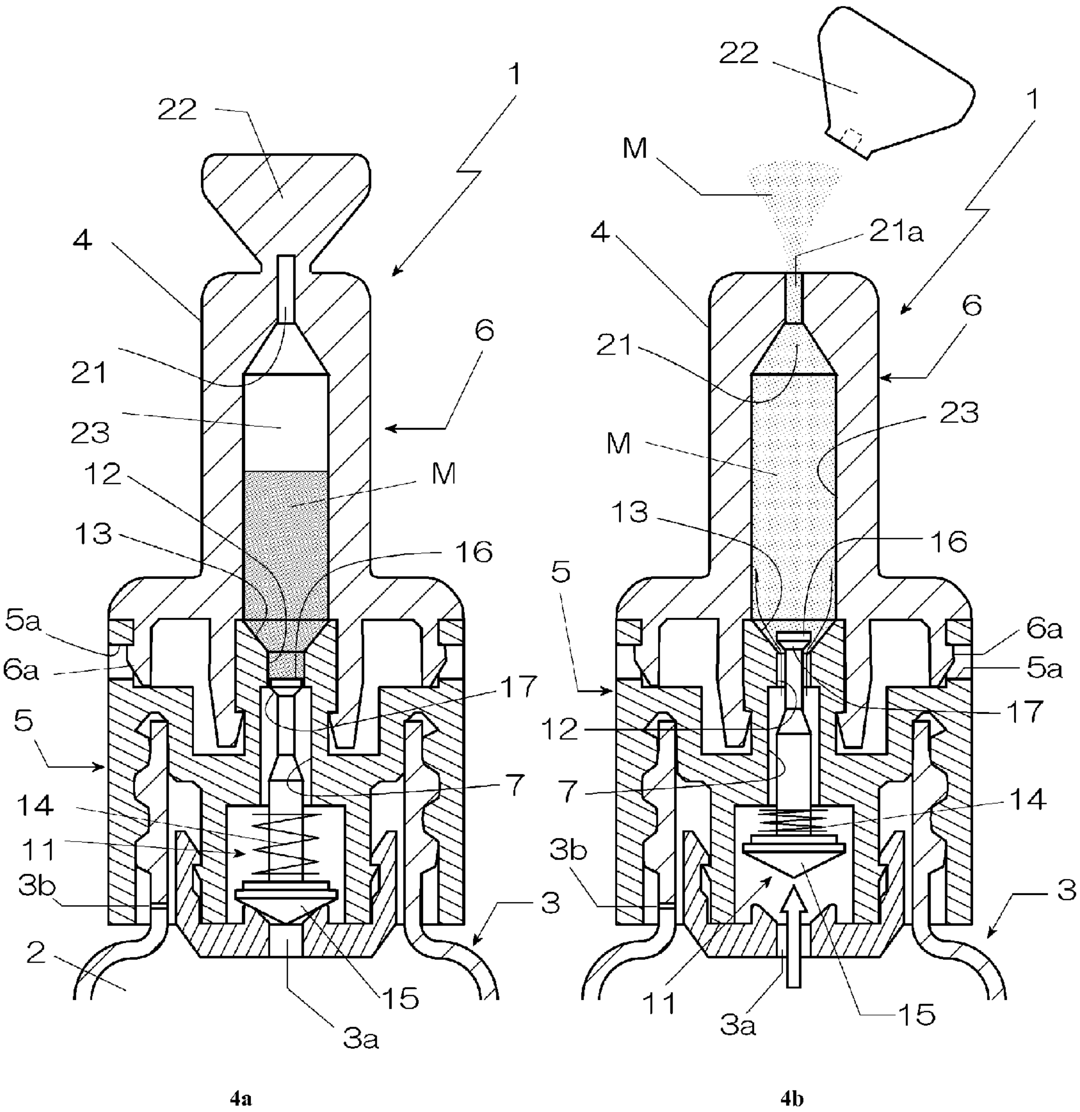
FIG. 4 illustrates an enlarged cross sectional view showing the main parts of the nasal spray applicator.

FIG. 4 illustrates two configurations of a nasal spray applicator device. FIG. 4*a* illustrates a first configuration, wherein a device is closed so that air cannot flow from the manual air pump (3), into a flow outlet (3*a*), and ultimately out of the nozzle hole (21*a*). In this embodiment, the closed configuration is provided by a spring (14) that is configured to keep a check valve (11) in a closed configuration and by a breakable cover (22) that is configured to block the flow of air out of the nozzle hole (21*a*). Thus, in the closed configuration, the nozzle (21) is a portion of the therapeutic reservoir (23). Typically, the material used for construction of the nozzle and breakable cover is strong enough to retain the shape of the nozzle hole (21*a*), but weak enough to be readily removed. This embodiment further provides a poppet (16) for inhibiting the downstream movement of a powdered therapeutic formulation (M) from a powdered therapeutic reservoir (23) into a valve assembly (5). In a second configuration, illustrated in FIG. 4*b*, a device is open so that air can flow through a device and ultimately out of the nozzle hole (21*a*). In this embodiment, the open configuration is provided by the removal of the breakable cover (22) and a flow of air from the manual pump (3) sufficient to open a check valve (11) and allow air to past a deflecting surface of a poppet (17) into a powdered therapeutic formulation reservoir (23) and ultimately out of the nozzle hole (21*a*). As is apparent from the description, the therapeutic reservoir (23) part of the airflow path from the deformable volume (2) (e.g., a manual pump) to the nozzle hole (21*a*) in the open configuration.

As described herein, a device can be configured to be a small size such that it can easily be stored, or transported. A device can be between about 1 and 100 $cm^3$ in volume, between about 5 and 90 $cm^3$ in volume, between about 10 and 80 $cm^3$ in volume, between about 25 and 80 $cm^3$ in volume, between about 50 and 100 $cm^3$ in volume, between about 1 and 50 $cm^3$ in volume, between about 5 and 75 $cm^3$ in volume, between about 1 and 25 $cm^3$ in volume, between about 5 and 50 $cm^3$ in volume, between about 10 and 50 $cm^3$ in volume, or between about 25 and 50 $cm^3$ in volume. A device can be at least about 5, 10, 25, 30, 40, 50, 50, 75, or 100 $cm^3$ in volume. A device can be less than about 250, 200, 175, 150, 125, 100, 75, 70, 65, 60, 55, or 50 $cm^3$ in volume. Similarly, a device can also be configured to be lightweight. For example, a device can have a total mass of between about 1 and about 50 grams, between about 5 and about 40 grams, between about 10 and about 35 grams, between about 10 and about 30 grams, between about 10 and about 25 grams, or between about 10 and about 20 grams. A device can have a total mass of less than about 100 grams, 90 grams, 80 grams, 75 grams, 70 grams, 65 grams, 60 grams, 55 grams, 50 grams, 45 grams, 40 grams, 35 grams, 30 grams, 25 grams, 20 grams, or 10 grams or less.

As described herein, a device can be configured to deliver a substantial fraction of a single dose of a powdered therapeutic formulation into the nostril of a subject. A device can be configured to deliver a substantial fraction of an amount of powdered therapeutic formulation residing within a device into the nostril of a subject. A powdered therapeutic formulation or a substantial fraction thereof can be delivered after a single engagement of a device. A powdered therapeutic formulation or a substantial fraction thereof can be delivered after multiple engagements of a device, such as for example 1, 2, 3, 4, 5, 6, 7, 8, 9, or 10 engagements. Multiple engagements of a device can constitute a single use of a device. The substantial fraction of powdered therapeutic delivered by a device encompasses at least 50%, 55%, 60%, 65%, 70%, 75%, 80%, 85%, 90%, 91%, 92%, 93%, 94%, 95%, 96%, 97%, 97.5%, 98%, 98.5%, 99%, 99.5%, 99.9%, 99.95%, or 100% of the amount of powdered medicine therapeutic such as the amount in a single dose or the amount residing in a device. In some instances, 60-95% of the amount of powdered composition is expelled from the device after the first engagement. In such instances, a second engagement can result in expulsion of substantially all of the powdered composition. The remainder of a 1% or less of the powdered composition in the device, typically as a residual powder on the walls of the chamber, constitutes delivery of substantially all of the powdered composition.

A. Nozzle

Provided herein are nozzles adapted to deliver a powdered therapeutic formulation to a nostril of a subject. In one embodiment, a nozzle is adapted to be placed partially or completely into the nostril of a subject during use. In another embodiment, a nozzle is adapted to be placed externally and adjacent to the nostril, totally or partially covering the opening of the nostril.

A nozzle disclosed herein is not limited to a particular shape. A nozzle can be of a uniform width such as in the shape of a cylinder, a cuboid, a rhombohedron, or a parallelepiped. A nozzle can also be a funnel or frustum shape, with a wide end and a narrow end. The shape of a nozzle is wider at the upstream end and narrower at the downstream end. Alternatively, the shape of a nozzle is wider at the downstream end and narrower at the upstream end. The widest and narrowest sections of a nozzle, however, cannot be at any end. For example, the widest section of a nozzle can be at any position along the upstream to downstream axis. In nozzles where the widest section is found mid-length along the axis, the widest section can function as a stop that prevents the nozzle from being inserted further into the nostril. In some embodiments, a nozzle is composed of two or more shapes such as any of the shapes provided herein. For example, a nozzle can include a cylinder shaped portion and a cone shaped portion.

A nozzle can be composed of a variety of polymers, plastics, rubber, silicones, metal, composites, any other materials described herein as suitable for use in the manufacture of a device applicator, or any other material suitable for use as an applicator nozzle. A nozzle can be made of one material or type of material. Alternatively, a nozzle can be composed two or more different materials or types of materials. All or a portion of a nozzle can be a biocompatible material, or a hypoallergenic material. In some embodiments, a nozzle is comprised of one or more of silicone, acrylates, polyethylenes, polyurethane, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

A nozzle can be composed partially or entirely of clear or translucent materials. The use of a clear or translucent nozzle allows for the visual inspection of the nozzle to ascertain whether there is appreciable residual powdered therapeutic formulation remaining in a reservoir after use. If, upon inspection, a subject notices that there is a substantial amount of residual formulation in a reservoir, the subject can engage an air source once or multiple times and then check by visual inspection of the clear or translucent nozzle to see if there was sufficient delivery. This process can be repeated as needed to ensure that an adequate dose is delivered.

A nozzle material can be a soft, pliable or malleable material such that the nozzle can conform to the shape of the nostril of a subject. Alternately, nozzle can be composed of rigid, substantially rigid, flexible, or substantially flexible materials, or a combination thereof. A nozzle can be a rigid material such as a polymer, plastic, silicone, metal, or a composite at one end, and a soft, malleable, or pliable material at another end, such as for example the end of the nozzle that is placed in the nostril. The soft, pliable, or malleable material can provide the advantage of reducing the likelihood of injury during contact between the nostril of a subject and the nozzle. This aspect can be useful if a device is used by a third party such as a doctor, a nurse, a nursing home attendant, an emergency medical technician, a paramedic, a parent, a guardian or other caregiver to deliver a powdered therapeutic formulation to a subject.

In some embodiments, a nozzle is of a size to substantially fit inside a nostril of a subject. For example, at least 10%, 20%, 25%, 30%, 40%, 50%, 60%, 70%, 75%, 80%, 90%, or 95% of the nozzle can fit inside the nostril of a subject during use of a device. Between about 5% and about 90% of the nozzle of a device can fit inside the nostril of a subject during use of a device. In other embodiments, between about 5% and 75%, 10% and 50%, 10% and 30%, 20% and 60% or 30% and 90% of the nozzle of a device can fit inside the nostril of a subject during use of a device.

The length of nozzle can be measured from an upstream end to a downstream end, where upstream and downstream denote the direction of air or other propellant during operation of a device. The upstream to downstream length of the nozzle can be less than about 5 cm, less than about 4.5 cm, less than about 4 cm, less than about 3.5 cm, less than about 3 cm, less than about 2.5 cm, less than about 2 cm, less than about 1.5 cm, or less than about 1.0 cm. The length of the nozzle can be between about 1 cm and 5 cm, between about 1 cm and 4 cm, between about 1 cm and 3 cm, between about 2 cm and 5 cm, or between about 2 cm and 4 cm in length.

In some embodiments, the width perpendicular to the upstream to downstream axis of the nozzle at its widest section is between about 1 cm to about 4 cm, 1 cm to about 3 cm, 1 cm to about 2 cm, 2 cm to about 4 cm, or 2 cm to about 3 cm. In some embodiments, the width perpendicular to the upstream to downstream axis of the nozzle at its widest section is no more than about 1 cm, 1.5 cm, 2 cm, 2.5 cm, 3 cm, 3.5 cm, 4 cm, 4.5 cm, or 5 cm wide. In some embodiments, the width perpendicular to the upstream to downstream axis of the nozzle at its narrowest section is no more than about 1.0 cm, 1.5 cm, 2.0 cm, 2.5 cm, or 3.0 cm. In some embodiments, the width perpendicular to the upstream to downstream axis of the nozzle at its narrowest section lies within the range of 0.5 cm to 3.0 cm; 1.0 to 2.5 cm or 1.0 to 2.0 cm.

The width of the nozzle can vary continuously, in a stepwise fashion or a combination thereof. The upstream and downstream ends of the nozzle can be the same width or different. In some embodiments, the narrowest end is the end that is placed in a nostril of a subject before administration. In some embodiments, the widest and narrowest sections of a nozzle are at the ends. For example, the widest section of a nozzle can be at the upstream end and the narrowest section of the nozzle can be at the downstream end, or vice versa. In some embodiment, the widest and/or narrowest sections of a nozzle are not at the end. In some embodiments, the widest section of a nozzle houses a powdered therapeutic formulation reservoir. The volume of a nozzle can be about 5 $cm^3$ or less, 4 $cm^3$ or less, 3 $cm^3$ or less, 2 $cm^3$ or less, or 1 $cm^3$ or less. In some embodiments, the volume of a nozzle is between about 5 $cm^3$ and about 1.0 $cm^3$, between about 4 $cm^3$ and about 1.0 $cm^3$, between about 3.0 $cm^3$ and about 1.0 $cm^3$, or between about 2 $cm^3$ and about 1.0 $cm^3$.

A nozzle can comprise a powdered therapeutic formulation reservoir adapted to contain a powdered therapeutic formulation for deliver into the nostril of a subject. In some instances, a powdered therapeutic reservoir is formed entirely by the nozzle. In other instances, a reservoir is formed in part by the nozzle and in part by a valve assembly of a device. For example, the downstream end of a reservoir can be formed by a nozzle, and the upstream end of a reservoir can be formed by a poppet or other portion of a valve assembly. FIG. 4B. In other embodiments, a reservoir is formed by the nozzle and a friable membrane. A reservoir can be an integral part of the nozzle in that it cannot be removed or replaced separately from removing or replacing the nozzle itself. A reservoir can be a separate replaceable, insertable, or removable part. In some embodiments, the replaceable, insertable, or removable reservoir takes the form of a capsule or cartridge. In some embodiments, the replaceable reservoir is not a capsule. In some embodiments, a valve assembly provides a powdered therapeutic reservoir. There can be a valve, a friable membrane, or other means for regulating the flow of air, propellant, or powdered therapeutic from a reservoir. There can be a valve, a friable membrane, or other means for regulating the flow of air, propellant, or powdered therapeutic into a reservoir. In some embodiments, a nozzle houses a separate powdered therapeutic formulation reservoir that is disposed within the nozzle adapted to contain a powdered therapeutic formulation for delivery into the nostril of a subject. A powdered therapeutic formulation reservoir can be external to a nozzle and can be in communication with the nozzle or valve assembly through an opening or a duct.

In some embodiments, a powdered therapeutic reservoir is about 5 $cm^3$ in volume or less, about 4 $cm^3$ in volume or less, 3 $cm^3$ in volume or less, 2 $cm^3$ in volume or less or 1 $cm^3$ in volume or less. In some embodiments, a reservoir is between about 1 $cm^3$ and 5 $cm^3$, between about 1.0 $cm^3$ and 4 $cm^3$, between about 1.0 $cm^3$ and 3 $cm^3$, between about 1.0 $cm^3$ and about 2 $cm^3$, between about 2 $cm^3$ and about 5 $cm^3$, or between about 2 $cm^3$ and about 4 $cm^3$ in volume. In some embodiments, a reservoir is suitable for storing a dose of a therapeutic formulation between about 10 mg and 2000 mg, between about 50 mg and 1500 mg, between about 100 mg and 1000 mg, between about 100 mg and 500 mg, between about 500 mg and 2000 mg, or between about 1000 mg and 2000 mg of a powdered therapeutic formulation. In some embodiments, a reservoir is suitable for storing at least 10 mg, 50 mg, 100 mg, 200 mg, 300 mg, 400 mg, 500 mg, 600 mg, 700 mg, 800 mg, 900 mg, 1000 mg, 1500 mg, or 2000 mg of a powdered therapeutic formulation. In some embodiments, a reservoir is suitable for storing at most 100 mg, 200 mg, 300 mg, 400 mg, 500 mg, 600 mg, 700 mg, 800 mg, 900 mg, 1000 mg, 1500 mg, or 2000 mg of a powdered therapeutic formulation. In some embodiments, a reservoir is configured to hold a single dose of a powdered therapeutic formulation while in other embodiments a reservoir is configured to hold multiple (2, 3, 4, 5, 6, 7, 8, 9, 10) doses of a powdered therapeutic formulation.

A reservoir can be filled with a powdered therapeutic formulation during manufacture of a device. A reservoir can be filled with a powdered therapeutic formulation prior to affixing or attaching a nozzle to a valve assembly or to an air source or a combination thereof. Alternatively, a reservoir can be filled after affixing or attaching a nozzle to a valve assembly or to an air source or a combination thereof.

A powdered therapeutic reservoir is not limited to any particular shape and can be disposed with a nozzle as a sphere, an ellipsoid, a cylinder, a cuboid, a frustum, or any other suitable shape such as any of the shapes described herein. In some embodiments, the shape of a reservoir is chosen to minimize the presence of corners, sharp edges, or other surface features that can disrupt airflow. In some embodiments, the shape of a reservoir is chosen to eliminate areas that do not experience uniform, laminar or high airflow during operation of a device. This can have the effect of reducing places within a reservoir and the nozzle where the therapeutic formulation can clump or accumulate and thereby lower the total amount of therapeutic formulation delivered to the nostril of the subject. For example, the shape of a medicine reservoir can be a frustum, or parallelepiped in which all corners have been rounded off. In some embodiments, a medicine reservoir is composed of two or more shapes such as any of the shapes provided herein. For example, a medicine reservoir can include a cylinder shaped portion and a cone shaped portion. Alternatively, by way of example only, a medicine reservoir can include two cone shaped portions joined at their widest ends or two cone shaped portions linked by an intervening cylinder shaped portion.

A nozzle can contain a flow restrictor adapted to restrict the flow of air through at least a portion of a device and thereby increase or decrease the velocity of, or redirect, the airflow within a device. In some embodiments, the flow restrictor is at the downstream end of the nozzle. The flow restrictor can be at the upstream end of the nozzle. There can be a flow restrictor at both the upstream and downstream end of a nozzle. In some embodiments, the flow restrictor is disposed at the downstream end of the nozzle and smoothly narrows in width from the upstream to the downstream end. Alternatively, the flow restrictor can narrow in a stepwise fashion, or can narrow in a combination of stepwise and continuously from the upstream to the downstream end. This can provide for increased velocity of air and/or powdered therapeutic from the nozzle into the nostril of the subject during operation of a device. In some embodiments, a flow restrictor disposed at the downstream end of a nozzle narrows down to a nozzle hole from which air and powdered therapeutic exits the nozzle during operation.

A flow restrictor can provide for the redirection of air or other propellant from along the inner walls of the nozzle and into the center of the airflow stream. A flow restrictor can be configured to direct the flow of air from along the inner walls of the nozzle in a laminar like fashion. A flow restrictor can be configured to direct the airflow into a powdered therapeutic reservoir in a turbulent fashion. A flow restrictor can be configured to provide a vortex in at least a portion of a powdered therapeutic formulation reservoir during use of a device. The redirected flow of air provided by the flow restrictor can break up at least a portion of aggregates or clumps of a powdery formulation present in a reservoir. The redirected flow of air can ensure that a substantial fraction of a powdered therapeutic present in a reservoir is delivered to the nostril of a subject during routine use of a device. For example, the redirected flow of air provided by a flow restrictor can turbulently mix and therefore effectively aerosolize a powdered therapeutic. A flow restrictor can be any of a number of shapes including but not limited to a cone, a cylinder, tapered cylinder, a frustum, and a parallelepiped or any other shape provided herein, including a combination of one or more shapes.

A flow restrictor can vary in width from slightly smaller than the width of a nozzle down to the width of a nozzle hole. For example, a flow restrictor can vary in width from at least 3 mm, 4 mm, 5 mm, 6 mm, 7 mm, 8 mm, 9 mm, 10 mm, 11 mm, 12 mm, 13 mm, 14 mm, or 15 mm at the widest part to less than 1 mm, 2 mm, 3 mm, 4 mm, 5 mm, 6 mm, 7 mm, 8 mm, 9 mm, or 10 mm at the narrowest section of the flow restrictor. A flow restrictor can be at its widest point between about 5 mm and about 15 mm wide, or between about 8 mm and 12 mm. A flow restrictor can be at its narrowest point between about 1 mm and about 10 mm wide, or between about 2 mm and 7 mm wide. A flow restrictor can have an upstream to downstream length of at least 20 mm, 15 mm, 10 mm, or 5 mm. A flow restrictor can be between about 5 mm and about 20 mm long, between about 5 mm and about 15 mm, or between about 5 mm and about 10 mm long.

A nozzle hole can be adapted to allow the exit of a powdered therapeutic formulation from the nozzle as a single stream. In some embodiments, a nozzle has multiple holes that emit the powdery formulation as a multiple stream that remain separate or that combine into a single stream. In some embodiments, a nozzle hole is disposed at the downstream end of the nozzle. In some embodiments, a nozzle hole is also the downstream end of the flow restrictor. A nozzle hole can be any of a number of shapes including but not limited to a circle, oval, triangle, rectangle, or combination thereof. In some embodiments, a nozzle is configured to provide a high velocity of propellant and/or powdered therapeutic into the nostril of a subject. For example, a nozzle can be configured to provide a peak propellant velocity of between about 1 m/s to about 10 m/s, about 2 m/s to about 8 m/s or about 3 m/s to about 6 m/s.

In some embodiments, the size of the nozzle hole when there is only one hole, when measured at its widest section, is less than 20 mm, less than about 15 mm, less than about 12 mm, less than about 10 mm, less than about 8 mm, less than about 5 mm, or less than about 3 mm. In embodiments where there is more than one nozzle hole the size of individual holes is less than 10 mm, less than about 8 mm, less than about 6 mm, less than about 5 mm, less than about 4 mm, less than about 3 mm, or less than about 2 mm.

In some embodiments, the upstream to downstream depth of a nozzle hole, that is the length of the channel formed from the surface of a nozzle at the site of the hole to the tip of a reservoir or flow restrictor, is less than about 50 mm, less than about 40 mm, less than about 30 mm, less than about 25 mm, less than about 20 mm, less than about 15 mm, less than about 10 mm, less than about 7 mm, less than about 5 mm, less than about 3 mm, or less than about 1 mm. In some embodiments, the surface of a nozzle at the site of the hole is the downstream top of a reservoir or flow restrictor effectively producing a depth of 0 mm.

A nozzle can also include a throat. A throat can be adapted to provide for a flow of air from a valve assembly to a therapeutic reservoir or a nozzle. In some embodiments, a throat is at the upstream end of a nozzle. A throat can additionally or alternatively be at the upstream end of a medicine reservoir. In some embodiments, a throat is a part of a nozzle. A throat can form the upstream end of a powdered therapeutic formulation reservoir. In some embodiments, a throat is disposed at the upstream end of a diffuser. In some embodiments, a throat is in communication with a diffuser which in turn is in communication with a powdered therapeutic reservoir, which is in turn in communication with a flow restrictor which is in turn in communication with a nozzle hole. In some embodiments, a throat is partially formed by a nozzle and partially formed by a valve assembly. In some embodiments, a throat is formed by a valve assembly.

A throat can be configured to provide for air or propellant egress from a valve assembly thereby allowing it to enter a nozzle and/or powdered therapeutic reservoir. In some embodiments, a throat is configured to house a poppet or a portion of a poppet such as a deflecting surface of a poppet. In some embodiments, a throat is configured to slidably house a poppet or a portion of a poppet such as a deflecting surface of a poppet. In some embodiments, a poppet disposed within a throat restrains a powdered therapeutic formulation inside a nozzle from moving upstream such as into a valve assembly. A throat can be any number of shapes including but not limited to a cone, a cylinder, tapered cylinder, a frustum, and a parallelepiped or any other shape provided herein, including a combination of one or more shapes.

In some embodiments, the upstream to downstream length of a throat is less than 20 mm, less than 15 mm, less than 12 mm, less than 11 mm, less than 10 mm, less than 9 mm, less than 8 mm, less than 7 mm, less than 6 mm, less than 5 mm, less than 4 mm, or less than 2 mm. In some instances, the upstream to downstream length of a throat is between about 2 mm and 20 mm, between about 5 mm and 15 mm, or between about 5 mm and 10 mm.

In some embodiments, the width perpendicular to the upstream to downstream axis of a throat at its widest section is between about 2 mm to about 10 mm, about 2 mm to about 8 mm, or about 2 mm to about 5 mm. In some embodiments, the width perpendicular to the upstream to downstream axis of a throat at its widest section is at least 1 mm, 2 mm, 3 mm, 4 mm, 5 mm, 6 mm, 7 mm, 8 mm, 9 mm, or 10 mm wide.

A nozzle can include a diffuser. A diffuser can be in communication with a powdered therapeutic reservoir and is adapted to direct a flow of air along the inner walls of a powdered therapeutic reservoir. In some embodiments, a diffuser is disposed at the upstream end of a powdered therapeutic reservoir and at the downstream end of a throat. In some embodiments, a diffuser is fabricated as a separate part that is joined to another part comprising a portion of a powdered therapeutic reservoir to create a complete reservoir. In other embodiments, a powdered therapeutic reservoir includes a built in diffuser and the whole unit is one piece. For example, the upstream portion of a powdered therapeutic reservoir can form a diffuser. Additionally, the upstream portion of a powdered therapeutic reservoir can form a diffuser and a throat.

A diffuser can be configured to allow air or other propellant from a valve assembly into a powdered therapeutic reservoir, such as for example, from a valve assembly through a throat. In some embodiments, a diffuser is configured to provide for a reduction in propellant velocity. In some embodiments, a diffuser is configured to smoothly transition air or other propellant flow from a throat to the inner walls of a powdered therapeutic reservoir. In some embodiments, a diffuser is configured to provide for airflow, for example laminar airflow along the inner walls of a powdered therapeutic reservoir (FIG. 4*b*, arrows). In some embodiments, laminar airflow increases the amount of therapeutic formulation in a reservoir that is aerosolized compared to that achieved with other types of airflow including turbulent airflow. In some embodiments, the use of laminar airflow for aerosolization of a therapeutic formulation increases the amount of a formulation that is delivered to a user compared to the amount of formulation delivered by other types of airflow. In some embodiments, a diffuser is configured to provide linear airflow, such as for example linear airflow along the inner walls of a powdered therapeutic reservoir.

Figure 6:
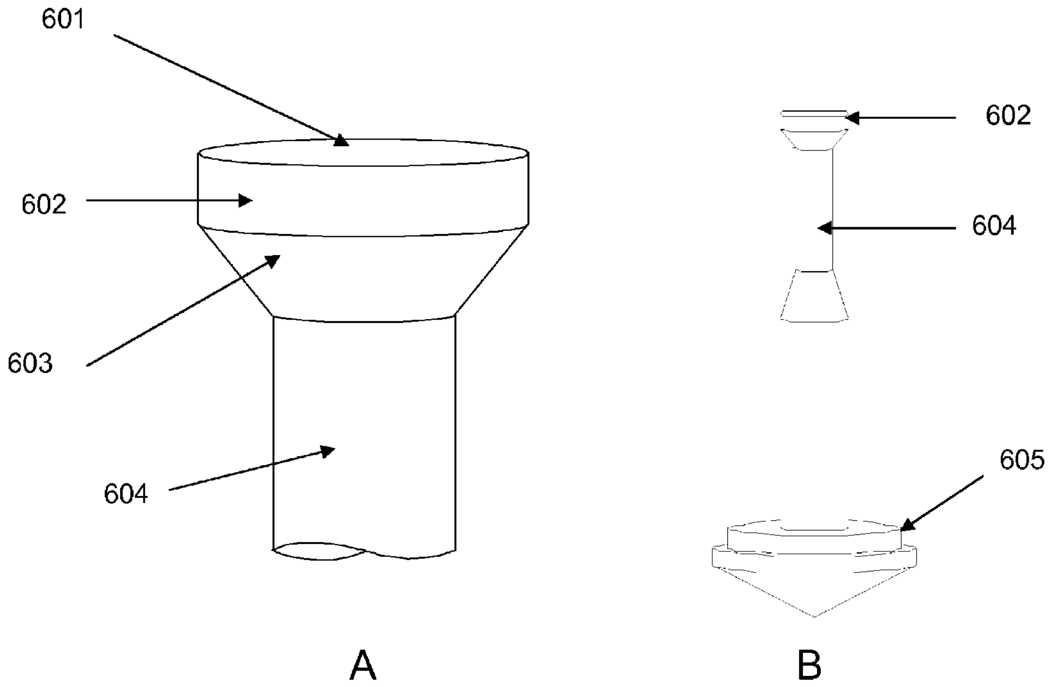
FIG. 6. Panel A illustrates an enlarged view of a deflecting surface (poppet head). Panel B illustrates a poppet attached to a stem that is in communication with a valve disk.

A diffuser can comprise a poppet. FIG. 6 shows expanded views of one embodiment of a poppet useful in the devices of the present disclosure. FIG. 6A illustrates a close up view of a deflecting surface (poppet head). FIG. 6B illustrates a poppet affixed to a stem that is further attached to a valve assembly. Generally a poppet will comprise a top surface (601) and a riser portion (602). The top surface (601) can be flat, concave or convex and, in some embodiments, when present in a device disclosed herein can serve as the bottom portion of a reservoir (FIG. 4*a*, 23) containing a therapeutic substance. A deflecting surface (603) is angled with respect to the shaft (604) and the riser portion (602). A deflecting surface can be any appropriate angle for directing airflow along the sides of the reservoir (FIG. 4*a*, 23). For example, the deflecting surface can be angled between 95-170 degrees with respect to the shaft, such as at about 95 degrees, about 100 degrees, about 105 degrees, about 110 degrees, about 115 degrees, about 120 degrees, about 125 degrees, about 130 degrees, about 135 degrees, about 140 degrees, about 145 degrees, about 150 degrees, about 155 degrees, about 160 degrees, about 165 degrees or about 170 degrees with respect to the shaft. Typically, the shaft (604) has a smaller diameter than the top surface (601) and the riser portion (602), allowing for the angling of the deflecting surface (603). Also, the shaft (604) is typically connected to a valve disk (605; FIG. 4*b*, 15). In some embodiments, a portion of a poppet such as, for example, a deflecting surface of a poppet (603) can be utilized in a device described herein. In some embodiments, a diffuser is configured to slidably house a poppet or a portion of a poppet such as, for example, a deflecting surface of a poppet. A diffuser can be any number of shapes including but not limited to a cone, a cylinder, tapered cylinder, a frustum, and a parallelepiped or any other shape provided herein, including a combination of one or more shapes.

In some embodiments, the upstream to downstream length of a diffuser is less than about 20 mm, 15 mm, 14 mm, 13 mm, 12 mm, 11 mm, 10 mm, 9 mm, 8 mm, 7 mm, 6 mm, 5 mm, 4 mm, 3 mm or 2 mm. In some embodiments, the length of a diffuser is between about 2 mm to 20 mm, 2 mm to 15 mm, 2 mm to 10 mm, 2 mm to 7 mm, or 2 mm to 5 mm.

The flow restrictor can vary in width from slightly smaller than the width of a nozzle down to the width of a nozzle hole. For example, a flow restrictor can vary in width from at least 3 mm, 4 mm, 5 mm, 6 mm, 7 mm, 8 mm, 9 mm, 10 mm, 11 mm, 12 mm, 13 mm, 14 mm, or 15 mm at the widest part to less than 1 mm, 2 mm, 3 mm, 4 mm, 5 mm, 6 mm, 7 mm, 8 mm, 9 mm, or 10 mm at the narrowest section of a flow restrictor. A flow restrictor can be at its widest point between about 5 mm and about 15 mm wide, or between about 8 mm and 12 mm. A flow restrictor can be at its narrowest point between about 1 mm and about 10 mm wide, or between about 2 mm and 7 mm wide. A flow restrictor can have an upstream to downstream length of at least 20 mm, 15 mm, 10 mm, or 5 mm. A flow restrictor can be between about 5 mm and about 20 mm long, between about 5 mm and about 15 mm, or between about 5 mm and about 10 mm long.

In some embodiments, the width perpendicular to the upstream to downstream axis of a diffuser at its widest is at least 3 mm, 4 mm, 5 mm, 6 mm, 7 mm, 8 mm, 9 mm, 10 mm, 11 mm, 12 mm, 13 mm, 14 mm, or 15 mm. A diffuser can also have a width at its narrowest section that is less than 1 mm, 2 mm, 3 mm, 4 mm, 5 mm, 6 mm, 7 mm, 8 mm, 9 mm, or 10 mm.

A nozzle can include a cover. A cover can be positioned at the downstream end of a nozzle. Alternatively, or in addition, a cover can be positioned at the downstream end of a nozzle hole. A cover can be configured to inhibit an unintentional discharge of a device. For example, a cover can be air tight preventing any airflow out of the downstream end of a nozzle and thereby preclude accidental engagement of an air source from leading to discharge of a powdered therapeutic. Such accidental engagements can occur by rough handling of a device such as during storage or shipping. A cover can also be configured to provide an environment suitable for storage of a powdered therapeutic within a powdered therapeutic reservoir. For example, a cover can inhibit or block the intrusion of outside air and/or water into a nozzle and thus inhibit or block the intrusion of air or water into a powdered medicine reservoir. A cover can be a replaceable cover, such that it can be removed and replaced. With a replaceable cap, a removable band can be employed to securely fasten a cap to a nozzle. Alternatively, a cover can be a breakable cover such that it is removed once by breaking from a nozzle. A cover can be a breakable tab, or a breakable membrane, or a cap.

A nozzle can further include means for attachment to a valve assembly. In some embodiments, a nozzle and a valve assembly comprise one continuous part. In other embodiments, a nozzle and a valve assembly can be formed as separate parts that are then attached together during manufacture or prior to use. A nozzle and valve assembly can be attached such that the upstream end of a nozzle is in communication with the downstream end of a valve assembly. In some embodiments, a nozzle and valve assembly is attached in a reversible fashion or a substantially permanent fashion such that it is difficult to separate a nozzle and valve assembly back into separate parts after manufacture. A means for attachment can include any means known in the art for attaching two objects together comprised of materials provided herein. For example, a nozzle can be glued or otherwise attached with an adhesive to a valve assembly. Alternatively, a nozzle can be welded or soldered to a valve assembly. A nozzle can comprise physical means for attachment such as one or more hooks, ratchets, or engaging holes. Similarly, hooks, ratchets or engaging holes can interact with corresponding hooks ratchets or engaging holes in a valve assembly. Means for attachment of a nozzle to a valve assembly can include a combination of any of means for attachment provided herein.

B. Valve Assembly

Devices described herein comprise at least one valve assembly. A valve assembly is configured to regulate the flow of air from an air source and into a nozzle of a device. A valve assembly can further be configured to regulate the movement of powdered therapeutic formulation. In some embodiments, a valve assembly is configured to block the movement of powdered therapeutic formulation in the upstream direction.

A valve assembly can be composed of a variety of polymers, plastics, rubber, silicones, metal, composites, any other materials described herein as suitable for use in the manufacture of a device applicator, or any other material suitable for use as an applicator valve assembly. A valve assembly can be made of one material or type of material. Alternatively, a valve assembly can be composed two or more different materials or types of materials. All or a portion of a valve assembly can be a biocompatible material, or a hypoallergenic material. A valve assembly can be composed of rigid, substantially rigid, flexible, or substantially flexible materials, or a combination thereof. In some embodiments, a valve assembly is comprised of one or more of paper, silicone, acrylates, polyethylenes, polyurethane, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

A valve assembly can comprise a diffuser. In further embodiments, a diffuser portion of a valve assembly comprises a poppet (FIG. 6). A diffuser as previously described is in communication with a powdered therapeutic reservoir. A portion of a diffuser can be formed by a valve assembly. A portion can be formed by a powdered therapeutic reservoir. In some embodiments, a diffuser is at the downstream end of a valve assembly. In some embodiments, a diffuser is disposed at the upstream end of a powdered therapeutic reservoir and at the downstream end of a throat. In some embodiments, a diffuser forms a part of a powdered therapeutic reservoir.

A valve assembly can include a throat. A throat is located at the downstream end of a valve assembly. A throat can additionally, or alternatively, be at the upstream end of a medicine reservoir. In some embodiments, a throat is disposed at the upstream end of a diffuser. In some embodiments, a throat is in communication with a diffuser which in turn is in communication with a powdered therapeutic reservoir, which is in turn in communication with a flow restrictor which is in turn in communication with a nozzle hole. In some embodiments a throat is partially formed by a nozzle and partially formed by a valve assembly.

A valve assembly can include a flow passage that is adapted to provide for the flow of air from an air source into a nozzle. A flow passage can further be adapted to house one or more of a check valve or a portion thereof, a poppet or a portion thereof, or a spring or a portion thereof. In some embodiments, a flow passage is at the upstream end of a throat. In other embodiments, a flow passage is at the upstream end of a diffuser. In still other embodiments, a flow passage is located at the upstream end of a nozzle and/or a powdered therapeutic reservoir.

A flow passage can be configured to house a poppet disposed therein. The upstream or downstream portion of a flow passage can be configured to house a poppet disposed therein. In some embodiments a flow passage is configured to slidably house a poppet disposed therein. In some embodiments, a flow passage is configured to slidably house a poppet disposed therein such that a poppet moves from a first position to a second position. In some embodiments, the first position is provided when a device is not engaged by a user, and the second position is provided when a device is engaged by a user to deliver a powdered therapeutic into a nostril or nasal cavity of a subject.

A flow passage can be configured to house a valve disk disposed therein. In some embodiments, the upstream portion of a flow passage is configured to house a poppet disposed therein. In some embodiments, a flow passage is configured to slidably house a valve disk disposed therein. In some embodiments, a flow passage is configured to slidably house a valve disk such that a valve disk moves from a first position to a second position. In some embodiments, the first position is provided when a device is not engaged by a user, and the second position is provided when a device is engaged by a user to deliver a powdered therapeutic into the nostril or nasal cavity of a subject. A flow passage can further be configured to house a means for maintaining a valve disk and/or poppet in the first position when a device is not engaged by a user and, in some embodiments, returning a valve disk from a second position back to a first position. Such means include, for example a spring, lever, or a stiff wire or arm A flow passage can contain a portion that houses a poppet or a portion of a poppet such as, for example, the stem of a poppet and portion which houses a valve disk. In some embodiments, the portion that houses a poppet is a different size or shape than the portion which houses a valve disk. A flow passage can be any number of shapes including but not limited to a cone, a cylinder, tapered cylinder, a frustum, and a parallelepiped or any other shape provided herein, including a combination of one or more shapes. In some embodiments, the portion of a flow passage that houses a poppet is narrower than the portion of a flow passage which houses a valve disk.

In some embodiments, the upstream to downstream length of a flow passage is less than about 20 mm, less than about 15 mm, less than about 12 mm, less than about 11 m, less than about 10 mm, less than about 9 mm, less than about 8 mm, less than about 7 mm, less than about 6 mm, less than about 5 mm, or less than about 4 mm. In some embodiments, the length of a flow passage is between about 4 mm and 20 mm, between about 4 mm and 15 mm, between about 4 mm and 12 mm, or between about 4 mm and 10 mm.

In some embodiments, the width perpendicular to the upstream to downstream axis of a flow passage at its widest section is between about 2 mm to about 15 mm, 2 mm to about 12 mm, 2 mm to about 10 mm, 2 mm to about 8 mm. In some embodiments, the width perpendicular to the upstream to downstream axis of a flow passage at its widest section is at least about 2 mm, 3 mm, 4 mm, 5 mm, 6 mm, 7 mm, 8 mm, 9 mm, 10 mm or 12 mm wide. In some embodiments, a flow passage has a width at its narrowest section that is less than about 2 mm, 3 mm, 4 mm, 5 mm, 6 mm, 7 mm, 8 mm, 9 mm, 10 mm or 12 mm wide.

The width of a flow passage can vary continuously, in a stepwise fashion or a combination thereof. The upstream and downstream ends of a flow passage can be of the same or different widths or shapes. In some embodiments, the narrowest end is the upstream end. In some embodiments, the narrowest end is the downstream end. In some embodiments, the widest and narrowest sections of a flow passage are at the ends. In other embodiments, the widest and/or narrowest sections of a flow passage are not at the end. In some instances, a flow passage is less than about 1.5 $cm^3$, 1 $cm^3$, 0.5 $cm^3$, 0.4 $cm^3$, 0.35 $cm^3$, 0.3 $cm^3$, 0.25 $cm^3$, 0.2 $cm^3$, 0.15 $cm^3$, or 0.1 $cm^3$ in volume.

A valve assembly can contain a flow outlet. In some embodiments, a flow outlet is at the upstream end of a flow passage. In some embodiments, a flow-outlet is positioned at the upstream end of a valve assembly. In some embodiments, a flow outlet is positioned at the downstream end of an air source. A flow outlet can alternatively, or in addition, be in communication with a valve disk or other means for preventing the flow of air from an air source into a valve assembly such as a frangible membrane. A flow outlet is configured to allow movement of air or propellant downstream from the air or propellant source, for example, a flow outlet can be configured to allow the movement of air downstream from an air source into a flow passage. In some embodiments, a flow outlet is configured to provide a velocity or pressure of air or propellant sufficient to rupture a frangible membrane directly or through the movement of a piercing member, or sufficient to move a valve disk from a first position to a second position during use. For example, a flow outlet can be configured to provide a pressure of between about 1 kilopascals to about 100 kilopascals, about 2 kilopascals to about 50 kilopascals, about 4 kilopascals to about 40 kilopascals or about 5 kilopascals to about 35 kilopascals. A flow outlet can be any of a number of shapes including but not limited to a cone, a cylinder, tapered cylinder, a frustum, and a parallelepiped or any other shape provided herein, including a combination of one or more shapes.

In some embodiments, the upstream to downstream length of a flow outlet is less than about 20 mm, less than about 15 mm, less than about 10 mm, less than about 8 mm, less than about 7 mm, less than about 6 mm, less than about 5 mm, less than about 4 mm, or less than about 3 mm. In some embodiments, the length of a flow outlet is between about 3 mm and 20 mm, between about 3 mm and 15 mm, between about 3 mm and 10 mm, or between about 5 mm and 10 mm.

In some embodiments, the width perpendicular to the upstream to downstream axis of a flow outlet at its widest section is between about 5 mm and about 20 mm, or about 5 mm and 15 mm. In some embodiments, the width perpendicular to the upstream to downstream axis of a flow outlet at its widest section is at least about 5 mm, 6 mm, 7 mm, 8 mm, 9 mm, 10 mm, 11 mm, 12 mm, 13 mm, 14 mm, 15 mm, or 20 mm wide. In some embodiments, the width perpendicular to the upstream to downstream axis of a flow outlet at its narrowest is less than about 4 mm, 5 mm, 6 mm, 7 mm, 8 mm, 9 mm, 10 mm, 11 mm, 12 mm, 13 mm, 14 mm, 15 mm, or 20 mm wide.

A valve assembly can include a check valve for regulating the flow of air from an air source to the nozzle. In some embodiments, a check valve is configured to provide an open position that allows the flow of air from an air source and to the nozzle and a closed position to block the flow of air from an air source to the nozzle. In some embodiments, the movement from the closed to the open position is completely or partially reversible, such as by gravity, pressure, airflow, a lever or spring mechanism, or a combination thereof. In other embodiments, the movement of a check valve from the open position to the closed position is not reversible or not readily reversible. In some embodiments, a check valve is a single use type valve such as a frangible membrane. In some embodiments, a check valve is configured to move from a first closed position to a second open position during use and move back from the open position to the closed position when a device is not in use. A valve can be regulated by a pressure differential between the pressure of air or other propellant at a flow outlet and the pressure of air or other propellant in a flow passage. A valve can be configured to remain in the open configuration in the presence of a sufficient flow or velocity of air from an air source and move to or maintain the closed configuration in the absence of a sufficient flow or velocity of air from an air source. In some embodiments, the closed configuration prevents the flow of air from an air source, and through a flow passage. In some embodiments, the closed configuration further prevents the flow of air into a nozzle and/or powdered therapeutic reservoir. In some embodiments, the open configuration allows the flow of air from an air source and through a flow passage. In some embodiments, the open configuration further allows the flow of air into a nozzle and/or powdered therapeutic reservoir and in some embodiments ultimately out of a nozzle hole.

A check valve can further prevent the flow of powdery therapeutic formulation into the air or propellant source. For example, when a pump is used as an air source, a check valve when in the closed position will prevent the flow of formulation into a pump when there is no airflow.

A valve assembly can include a poppet. In some embodiments, a poppet is a component of a check valve. In other embodiments, a poppet is a separate component from a check valve. In some embodiments, a poppet is disposed within a flow passage. In some embodiments, a poppet is disposed within a throat. In some embodiments, a poppet is disposed within a diffuser. In some embodiments, a poppet is disposed within one or more of a flow passage, throat, and diffuser. In some embodiments, a poppet is configured to adopt a first position and a second position. In some embodiments, the second position is the position of a poppet during use of a device to deliver powdered therapeutic and the first position is the position of a poppet when a device is not in use. In some embodiments, the first position inhibits the flow of air from an air source and/or valve assembly into a nozzle. In some embodiments, the second position allows the flow of air from an air source and/or valve assembly into a nozzle. In some embodiments, the movement of a poppet from the first position to the second position is reversible, such as by gravity, pressure, airflow, a lever or spring mechanism, or a combination thereof. In other embodiments, the movement of a poppet from the first position to the second position is not reversible or not readily reversible. The position of a poppet can be regulated by a pressure differential between the pressure of air or other propellant at a flow outlet and the pressure of air or other propellant in a flow passage. In some embodiments, a poppet is configured to remain in the second position in the presence of a sufficient flow or velocity of air from an air source and move to the first configuration in the absence of a sufficient flow or velocity of air from an air source.

A poppet can be configured to inhibit the upstream movement of powdered therapeutic from a reservoir into a valve assembly. In some embodiments, a poppet is configured to inhibit the upstream movement of powdered therapeutic from a reservoir into a valve assembly due to its position within a flow passage, throat and/or diffuser. For example, a poppet or a portion thereof can slidably force fit into a throat, whereby powdered medicine cannot move past a poppet from a reservoir and into a valve assembly. In another example, a poppet can comprise an O-ring, gasket, adhesive, or other means for sealing the interface between at least a portion of a poppet and at least a portion of one or more of a flow passage, throat or diffuser. In some embodiments, a sealing means is permanent or substantially permanent such that under normal manufacture, shipping, storage or operating conditions it remains intact and functional. In other embodiments, a sealing means is not permanent. For example, a sealing means can be configured to provide a sealing function until use, at which time a sealing function is broken. For example, a friable membrane can be overlaid on a poppet to prevent the egress of powdery formulation. When a poppet is activated, the friable membrane is ruptured. In some embodiments, a poppet also functions as a piercing element. In still other embodiments, a sealing means is reversible in that during use there is no seal, whereas before and after use, the seal between at least a portion of one or more of a flow passage, throat or diffuser is intact. A poppet can inhibit the upstream movement of powdered therapeutic in the first position and not the second position. In other embodiments, a poppet can inhibit the upstream movement of powdered therapeutic in the first position and in the second position.

A poppet can be any number of shapes including but not limited to a disc, an annulus, a torus, a cone, a cylinder, tapered cylinder, a frustum, a cuboid, and a parallelepiped or any other shape provided herein, including a combination of one or more shapes. A poppet can have a narrow end and a wide end. A poppet can be a uniform width. In some embodiments, the widest portion of a poppet cannot lie at the upstream or downstream end. In some embodiments, the narrowest portion of a poppet cannot lie at the upstream or downstream end.

In some embodiments, the upstream to downstream length of a poppet can be less than about 20 mm, less than about 15 mm, less than about 14 mm, less than about 13 mm, less than about 12 mm, less than about 11 mm, less than about 10 mm, less than about 9 mm, or less than about 8 mm, less than about 7 mm, less than about 6 mm, or less than about 5 mm. The length of a poppet can be between about 5 mm and 20 mm, between about 5 mm and 15 mm, or between about 5 mm and 10 mm.

In some embodiments, the width perpendicular to the upstream to downstream axis of a poppet at its widest section is between about 1 mm to about 10 mm, or about 1 mm to about 5 mm. In some embodiments, the width perpendicular to the upstream to downstream axis of a poppet at its widest section is no more than about 1 mm, 2 mm, 3 mm, 4 mm, 5 mm, 6 mm, 7 mm, 8 mm, 9 mm, or 10 mm wide. In some embodiments, a poppet has a width at its narrowest section that is no more than about 0.5 mm, 1 mm, 2 mm, 3 mm, 4 mm, 5 mm, 6 mm, 7 mm, 8 mm, or 9 mm wide, or 10 mm wide.

A poppet can include a stem (FIG. 6, 604). In some embodiments, a stem is disposed at the downstream end of a poppet. In other embodiments, a stem is at the upstream end of a poppet. In still other embodiments, a stem can comprise the middle or upstream portion of a poppet. In yet other embodiments, a stem can be positioned anywhere between the upstream and downstream ends of a poppet, such as for example half way between the ends, or about ⅓ or ¼ of the way from one end (upstream or downstream) to the other end of a poppet. In some embodiments, a stem is affixed to the upstream end of a deflecting surface (603). A stem can be disposed in a flow outlet, flow passage, a diffuser, or a throat. In some embodiments, a stem or a portion thereof is disposed within one or more of a flow outlet, flow passage, a diffuser, or a throat. In some embodiments, a stem is in communication with a flow outlet. A stem can slidably force-fit into a throat. A stem can comprise an O-ring, gasket, adhesive, or other means for sealing the interface between at least a portion of a stem and at least a portion of one or more of a flow outlet, flow passage, throat or diffuser. In some embodiments, a sealing means is permanent or substantially permanent such that under normal manufacture, shipping, storage or operating conditions it remains intact and functional. In other embodiments, a sealing means is not permanent. For example, a sealing means can be configured to provide a sealing function until use, at which time a sealing function is broken. In still other embodiments, a sealing means is reversible in that during use there is no seal, whereas before and after use, the seal between at least a portion of one or more of a flow outlet, flow passage, throat or diffuser is intact.

A stem can be configured to adopt a first position and a second position. In some embodiments, the first position is a closed configuration (e.g., FIG. 4*a*) which prevents the flow of air from an air source, and in some embodiments, through a flow passage, throat, and/or diffuser. In some embodiments, the first position further prevents the flow of air into a nozzle and/or powdered therapeutic reservoir. In some embodiments, a stem of a poppet in the first position is disposed in a throat or a flow passage such that air cannot flow from a flow passage into a throat and therapeutic formulation cannot flow upstream from a reservoir into a valve assembly. In some embodiments, a stem of a poppet in the first position is in communication with a flow outlet such that air cannot flow from a flow outlet into a flow passage. In some embodiments, the second position of a stem is an open configuration (e.g., FIG. 4*b*) which allows the flow of air from an air source and through a flow passage. In some embodiments, the second position further allows the flow of air into a nozzle and/or powdered therapeutic reservoir and in some embodiments ultimately out of a nozzle hole. A stem of a poppet or a portion thereof in the second position can be disposed with a flow outlet, flow passage, throat, and/or diffuser such that air can flow from a flow outlet, through a flow passage, and into a throat, a diffuser, and a reservoir, and then out of a nozzle hole.

In some embodiments, the movement of a stem from the first position to the second position can be reversible, such as by gravity, pressure, airflow, a lever or spring mechanism, or a combination thereof. In other embodiments, the movement of a stem from the first position to the second position is not reversible or not readily reversible. In some embodiments, the position of a stem is regulated by a pressure differential between the pressure of air or other propellant at a flow outlet and the pressure of air or other propellant in a flow passage. A stem can be configured to remain in the second position in the presence of a sufficient flow or velocity of air from an air source and move to the first configuration in the absence of a sufficient flow or velocity of air from an air source.

A stem of a poppet can be any number of shapes including but not limited to a disc, an annulus, a torus, a cone, a cylinder, tapered cylinder, a frustum, a cuboid, and a parallelepiped or any other shape provided herein, including a combination of one or more shapes. A stem can have a narrow end and a wide end. In some embodiments, the widest portion of a stem cannot lie at the upstream or downstream end. In some embodiments, the narrowest portion of a stem cannot lie at the upstream or downstream end. A stem can be a uniform width.

In some embodiments, the upstream to downstream length of a stem is less than about 20 mm, less than about 15 mm, less than about 14 mm, less than about 13 mm, less than about 12 mm, less than about 11 mm, less than about 10 mm, less than about 9 mm, less than about 8 mm, less than about 7 mm, less than about 6 mm, or less than about 5 mm. In some embodiments, the length of a stem is between about 5 mm and 20 mm or between about 5 mm and 10 mm.

A device as described herein can include a deflecting surface (e.g., FIG. 6, 603). In some embodiments, a deflecting surface is a component of a poppet. In other embodiments, a deflecting surface is a separate component from a poppet. In some embodiments, a deflecting surface is a component of a valve assembly. In other embodiments, a deflecting surface is a component of a nozzle. In some embodiments, a deflecting surface is disposed within a medicine reservoir. In some embodiments, a deflecting surface is disposed at, or affixed to, the downstream end of a poppet. In other embodiments, a deflecting surface is at the upstream end of a poppet. In still other embodiments, a deflecting surface can be anywhere between the upstream and downstream ends of a poppet, such as for example half way between the ends, or about ⅓ or ¼ of the way from one end (upstream or downstream) to the other end of a poppet.

A deflecting surface can be configured to adopt a first position and a second position, or a deflecting surface can be configured with a fixed position. In some embodiments, the first position is a closed configuration which prevents the flow of air from an air source, and through a flow passage, throat, and/or diffuser. In some embodiments, the first position further prevents the flow of air into a nozzle and/or powdered therapeutic reservoir. In some embodiments, a deflecting surface in the first position is disposed in a throat, a diffuser, or a flow passage, such that air cannot flow from a flow passage into a throat and a therapeutic formulation cannot flow upstream from a reservoir into a valve assembly. In some embodiments, the second position of a deflecting surface is an open configuration which allows the flow of air from an air source and through a flow passage. In some embodiments, the second position further allows the flow of air into a nozzle and/or powdered therapeutic reservoir.

The movement of a deflecting surface from the first position to the second position can be reversible (e.g., FIG. 5), such as by gravity, pressure, airflow, a lever or spring mechanism, or a combination thereof. In other embodiments, the movement of a deflecting surface from the first position to the second position is not reversible or not readily reversible. In some embodiments, the position of a deflecting surface is regulated by a pressure differential between the pressure of air or other propellant at a flow outlet and the pressure of air or other propellant in a flow passage. In some embodiments, a deflecting surface can be configured to remain in the second position in the presence of a sufficient flow or velocity of air from an air source and move to the first configuration in the absence of a sufficient flow or velocity of air from an air source.

A deflecting surface can be configured to direct a flow of air along the inner walls of a medicine reservoir. In some embodiments, a deflecting surface is configures to create a vortex of airflow in a medicine reservoir. In some embodiments, a deflecting surface is configured to direct a linear flow of air along the inner walls of a medicine reservoir. In some embodiments, a deflecting surface is configured to direct a laminar flow of air along the inner walls of a medicine reservoir. In some embodiments, a deflecting surface is configured to direct a flow of air along the inner walls of a medicine reservoir when a deflecting surface is in the second position. Additionally, or alternatively, a deflecting surface can be configured to direct a flow of air along the inner walls of a medicine reservoir in the first position. A device with a deflecting surface in a fixed position a deflecting surface in the fixed position can be configured to direct a flow of air along the inner walls of a medicine reservoir.

A deflecting surface can be any number of shapes including but not limited to a disc, an annulus, a torus, a cone, a cylinder, tapered cylinder, a frustum, a cuboid, and a parallelepiped or any other shape provided herein, including a combination of one or more shapes. A deflecting surface can have a narrow end and a wide end. A deflecting surface can be a uniform width. In some embodiments, the widest portion of a deflecting surface cannot lie at the upstream or downstream end. In some embodiments, the narrowest portion of a deflecting surface cannot lie at the upstream or downstream end.

A valve assembly can include a valve disk that regulates the movement of air from an air source into a flow passage. In some embodiments, a valve disk is a component of a poppet. In some embodiments, a valve disk is a separate component from a poppet. In some embodiments, a valve disk is affixed to or part of the upstream end of a poppet, such as the upstream end of a stem of a poppet, for example. In still other embodiments, a valve disk comprises the middle or upstream portion of a poppet. A valve disk can be positioned anywhere between the upstream and downstream ends of a poppet, such as for example half way between the ends, or about ⅓ or ¼ of the way from one end (upstream or downstream) to the other end of a poppet. In some embodiments, a valve disk is affixed to the upstream end of a deflecting surface. A valve disk can be disposed in a flow outlet, flow passage, a diffuser, or a throat. In some embodiments, a valve disk or a portion thereof is disposed within one or more of a flow outlet, flow passage, a diffuser, or a throat. In some embodiments, a valve disk is in communication with a flow outlet.

A valve disk can be in communication with a spring, lever, or flexible arm so as to provide a bias or force for sealing the interface between at least a portion of a valve disk and at least a portion of one or more of a flow outlet, flow passage, throat or diffuser. In some embodiments, a sealing of the interface between at least a portion of a valve disk and at least a portion of one or more of a flow outlet, flow passage, throat or diffuser valve disk can be accomplished by the use of an o-ring, gasket, adhesive, or other suitable means. In some embodiments, a sealing means is permanent or substantially permanent such that under normal manufacture, shipping, storage or operating conditions it remains intact and functional. In other embodiments, a sealing means is not permanent. For example, a sealing means can be configured to provide a sealing function until use, at which time a sealing function is broken. In still other embodiments, a sealing means is reversible in that during use there is no seal, whereas before and after use, the seal between at least a portion of one or more of a flow outlet, flow passage, throat or diffuser is intact.

A valve disk can be configured to adopt a first position and a second position. In some embodiments, the first position is a closed configuration which prevents the flow of air from an air source, and in some embodiments, through a flow outlet, flow passage, throat, and/or diffuser. In some embodiments, the first position further prevents the flow of air into a nozzle and/or powdered therapeutic reservoir. In some embodiments, a valve disk in the first position is configured such that air cannot flow from a flow outlet and therapeutic formulation cannot flow upstream from a reservoir into a valve assembly. In some embodiments, a valve disk in the first position is in communication with a flow outlet such that air cannot flow from a flow outlet into a flow passage. In some embodiments, the second position of a valve disk is an open configuration which allows the flow of air from an air source, out of a flow outlet, and through a flow passage and/or powdered therapeutic reservoir.

The movement of a valve disk from the first position to the second position can be reversible, such as by gravity, pressure, airflow, a lever or spring mechanism, or a combination thereof. In other embodiments, the movement of a valve disk from the first position to the second position is not reversible or not readily reversible. In some embodiments, the position of a valve disk can be regulated by a pressure differential between the pressure of air or other propellant at a flow outlet and the pressure of air or other propellant in a flow passage. In some embodiments, a valve disk can be configured to remain in the second position in the presence of a sufficient flow or velocity of air from an air source and move to the first configuration in the absence of a sufficient flow or velocity of air from an air source.

A valve disk can be any number of shapes including but not limited to a disc, an annulus, a torus, a cone, a cylinder, tapered cylinder, a frustum, a cuboid, and a parallelepiped or any other shape provided herein, including a combination of one or more shapes. In some embodiments, a valve disk can have a narrow end and a wide end. In some embodiments, a valve disk can be a uniform width. In some embodiments, the widest portion of a valve disk cannot lie at the upstream or downstream end. In some embodiments, the narrowest portion of a valve disk cannot lie at the upstream or downstream end.

In some embodiments, the upstream to downstream length of a valve disk is be less than about 10 mm, less than about 7 mm, less than about 5 mm, less than about 4 mm, less than about 3 mm, or less than about 2 mm. In some embodiments, the length of a valve disk can be between about 10 mm and 2 mm, or between about 5 mm.

In some embodiments, the width perpendicular to the upstream to downstream axis of a valve disk at its widest section is between about 4 mm to about 20 mm, or between 4 mm to about 10 mm. In some embodiments, the width perpendicular to the upstream to downstream axis of a valve disk at its widest section is at least about 4 mm, 5 mm, 6 mm, 7 mm, 8 mm, 9 mm, 10 mm, 11 mm, 12 mm, 13 mm, 14 mm, or 15 mm.

A valve assembly can include a spring, lever, arm, wire or other means for maintaining a device in a closed configuration when a device is not in use. A valve assembly can further include a spring, lever, arm, wire or other means for returning a device to a closed configuration from an open configuration after a device has been used. A spring, lever, arm, wire or other means can regulate the movement of one or more of a check valve, poppet, stem, deflecting surface, or valve disk from an open configuration to a closed configuration, or from a closed configuration to an open configuration, or from a first position to a second position, or from a second position to a first position. A spring can comprise a spring constant between about 0.10 to about 10 grams per millimeter, about 0.20 to about 5 grams per millimeter or about 0.5 to about 2 grams per millimeter. A spring or other means can maintain the closed position until the pressure differential between a flow outlet and a flow passage reaches between about 1 kilopascals to about 20 kilopascals or about 2 to about 10 kilopascals. A spring or other means can allow an open position in the presence of a velocity of air out of a flow outlet of between about 1 to 50 meters per second or about 2 to about 25 meters per second. A spring or other means can be configured to regulate the movement of a device from the closed configuration to the open configuration upon application of about 0.1 millinewtons to about 1.0 millinewtons, about 0.2 millinewtons to about 0.80 millinewtons, or about 0.4 millinewtons to about 0.6 millinewtons of force to one or more of a check valve, poppet, stem, deflecting surface, or valve disk. A spring or other means can be configured to regulate the movement of a device from the closed configuration to the open configuration upon the application of between about 1 to about 75, about 1 to about 50, about 2 to about 40, or about 5 to about 30 kilopascals of pressure on an air source of a device described herein.

A valve assembly can comprise a rigid backing disposed over at least a portion of an air source. A rigid backing can be configured to enable manual application of compressive force onto an air source. For example, a rigid backing can be configured to enable compressing an air source against a rigid backing between one or more fingers, such as the thumb and forefinger. A rigid backing can be disposed over at least about 5%, 10%, 15%, 20%, 25%, 30%, 35%, 40%, 45%, 50%, 55%, 60%, 65%, 70% or more of the surface area of an air source.

A valve assembly can include means for attachment to a nozzle as previously described. Additionally, a valve assembly can further include means for attachment to an air source. In some embodiments, an air source and a valve assembly can comprise one continuous part. An air source and a valve assembly can be formed as separate parts that are then attached together during manufacture or prior to use. An air source and valve assembly can be attached such that the downstream end of an air source is in communication with the upstream end of a valve assembly. In some embodiments, an air source and valve assembly can be attached in a reversible fashion or a substantially permanent fashion, such that it is difficult separate an air source and valve assembly back into separate parts after manufacture. Means for attachment can include any means known in the art for attaching two objects together comprised of materials provided herein. For example, a valve assembly can be glued or otherwise attached with an adhesive to an air source. Alternatively, a valve assembly can be welded or soldered to an air source. A valve assembly can comprise physical means for attachment such as a screw mechanism, one or more hooks, ratchets, or engaging holes. Similarly, hooks, ratchets or engaging holes can interact with corresponding hooks ratchets or engaging holes in an air source. Means for attachment of a valve assembly to an air source can include a combination of any of means for attachment provided herein.

C. Air Source

A device described herein can comprise an air source. An air source is configured to provide a flow of air or other propellant or a combination thereof through a powdered therapeutic formulation reservoir, out of a nozzle and into a nostril or nasal cavity of a subject. An air source can be configured to provide a flow of air into a valve assembly which regulates the flow of air into a nozzle or reservoir.

An air source can be composed of a variety of polymers, plastics, rubber, silicones, metal, composites, any other materials described herein as suitable for use in the manufacture of a device applicator, or any other material suitable for use as an applicator air source. An air source can be made of one material or type of material. Alternatively, an air source can be composed two or more different materials or types of materials. In some embodiments, all or a portion of an air source can be a biocompatible material, or a hypoallergenic material. An air source can be composed of rigid, substantially rigid, flexible, or substantially flexible materials, or a combination thereof. In some embodiments, an air source is comprised of one or more of silicone, acrylates, polyethylenes, polyurethane, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

An air source can be one of a variety of air sources suitable for use in a nasal applicator such as for example an air sources described in U.S. patent application Nos. US20090025720, US20090064997, US20080819617, US20080161771, US20080289629, US20080142018, US20070129665, US20060219240, US20060024185, US20060254585, US20040187868, US20040149289, US20040112378, US20020174865, U.S. Pat. No. 3,856,185, U.S. Pat. No. 4,017,007, U.S. Pat. No. 4,200,099, U.S. Pat. No. 5,046,493, U.S. Pat. No. 5,683,361, U.S. Pat. No. 5,702,362, U.S. Pat. No. 6,488,648, U.S. Pat. No. 6,824,080, U.S. Pat. No. 6,866,039, U.S. Pat. No. 6,938,798, U.S. Pat. No. 6,186,141, U.S. Pat. No. 6,345,737, U.S. Pat. No. 6,585,172, U.S. Pat. No. 6,543,448, U.S. Pat. No. 6,089,228, U.S. Pat. No. 6,427,680, U.S. Pat. No. 6,644,305, U.S. Pat. No. 6,494,204, U.S. Pat. No. 6,290,667, U.S. Pat. No. 7,481,218, international patent applications WO2002/00282, WO2005/000477, WO2008/026730, WO2007/102089, WO1990/07351, and WO/2003/000310, European patent Nos. EP1673123, and EP1390091, and Japanese patent and application Nos. JP2006122189, JP2001095918, JP3678955, JP11226127, JP3488624, JP11221280, JP11197245, JP3547605, JP10028735, JP9248342, JP09028805, JP08322934, JP08280808, JP8206208, JP8103499, and JP8071152 all of which are herein incorporated by reference in their entirety.

An air source can be a pressurized container. In some embodiments, a pressurized container contains air or other propellant such as one or more of a low molecular weight hydrocarbon such as butane or propane, dimethyl ether, methyl ethyl ether, nitrous oxide, carbon dioxide, nitrogen, a hydrofluorocarbon, compressed air, a chlorofluorocarbon, or a hydrofluoroalkane such as for example, 1,1,2,-tetrafluoroethane or 1,1,1,2,3,3,3-heptafluoropropane. A pressurized container can contain between about 0.1 g of propellant and about 5 g of propellant including at least about 4 g, 3 g, 2 g, 1.5 g, 1 g, 0.75 g, 0.5 g, 0.25 g, 0.2 g, or about 0.1 g of propellant. A pressurized container can be configured to contain a propellant at a maximum pressure of at least about 1.5 atm, 2 atm, 2.5 atm, 3 atm, 3.5 atm, 4 atm, 4.5 atm, 5 atm, 5.5 atm, 6 atm, 7 atm, 8 atm, 9 atm, 10 atm, 11 atm, or about 12 atm. In some embodiments, a pressurized container can be configured to contain a propellant at a maximum pressure of between about 2 atm and about 10 atm, 3 atm and about 9 atm, 4 atm and about 8 atm, 4 atm and about 7 atm, or between about 4 atm and about 6 atm.

A pressurized container can be activated to release propellant by any means known in the art. For example a pressure valve can engage an air source to release propellant upon the application of a compressive force, or a lever can engage an air source to release propellant upon movement of the lever. In another example, a pressurized container can be activated to release propellant in response to a digital or analog signal. For example, a user can push a button which controls the release of propellant such as by controlling a servo motor or a microprocessor controlled valve. In some embodiments, a container can be activated by a mechanism that detects nasal inhalation. For example, a lever or other sensing means such as a pressure sensor can be activated by positioning a device as described herein into the nostril of a subject and the inhalation of the subject. A pressurized container can be configured to release a controlled or metered amount of propellant each time a container is activated. In other embodiments, a pressurized container can continue to release propellant until a user has ceased to provide an activation input.

An air source can be a pump such as an electric pump or a manual pump. An air source can comprise an inner container slidably disposed within an outer container. Movement of one or more of inner and outer containers by manual or other means can provide a flow of air out of an air source and into a flow passage. Inner and outer containers of a pump can be configured to return to a resting state in the absence of an external compressive force, such as for example through the action of a spring or other return mechanism. In another example, a pump comprises a slidable piston. A piston can be actuated by manual or electric means. Movement of a piston by manual or other means can provide a flow of air out of an air source and into a flow passage. A piston can be configured to return to a resting state in the absence of an external force, such as for example through the action of a spring or other return mechanism.

A pump can comprise a deformable volume. For example, a pump can comprise a plastic, rubber or other deformable material. A pump can also comprise an articulated volume such that accordion-like folds allow compression of a pump to deliver air. A deformable volume can be compressed by for example one or more fingers, or by one or more hands. Alternatively, a deformable volume can be compressed by electronic or hydraulic means. In some embodiments, a deformable volume is compressed such as by application of a squeezing or other compressive force and can revert to a non-compressed shape upon release of the compressive force. In some embodiments, the reversion to a non-compressed shape can be provided by an inherent elastomeric force of the shape and materials of a deformable volume. The reversion can be assisted by a spring or other energy return mechanism.

An air source can be any shape suitable for use in a device described herein, including but not limited to a sphere, an ellipsoid, a cylinder, a cuboid, a frustum, or any other suitable shape such as any of the shapes described herein, or a combination thereof. The upstream to downstream length of an air source can be less than about 10 cm, 9 cm, 8 cm, 7 cm, 6 cm, 5 cm, 4.5 cm, 4 cm, 3.5 cm, 3 cm, or 2 cm. In some embodiments, the length of an air source can be between about 2 ccm and 10 cm, between about 2 cm and 8 cm, between about 2 cm and 5 mm, between about 4 cm and 10 cm, or between about 4 cm and 6 cm.

In some embodiments, the width perpendicular to the upstream to downstream axis of an air source at its widest section is less than 1 cm, 1.5 cm, 2 cm, 2.5 cm, 3 cm, 3.5 cm, 4 cm, 4.5 cm, 5 cm, 6 cm, 7 cm, 8 cm, 9 cm, 10 cm, 12 cm, 15 cm, or 20 cm wide.

In some embodiments, an air source has a volume that is less than 10 $cm^3$, 9 $cm^3$, 8 $cm^3$, 7 $cm^3$, 6 $cm^3$, 5 $cm^3$, 4 $cm^3$, 3 $cm^3$, 2 $cm^3$, or 1 $cm^3$. In some embodiments, an air source comprises a volume of between about 1 $cm^3$ and about 10 $cm^3$, or between about 2 $cm^3$ and about 10 $cm^3$, 2 $cm^3$ and about 7 $cm^3$, or 4 $cm^3$ and about 8 $cm^3$.

An air source can be configured to deliver between about 1 ml to about 10 ml of air or other propellant to a nostril of a subject during a single activation. An air source can be configured to deliver between about 1 ml to about 10 ml of air or other propellant to a powdered therapeutic reservoir of a device during a single activation. In some embodiments, an air source is configured to deliver at least 1 mL, 2 mL, 3 mL, 4 mL, 5 mL, 6 mL, 7 mL, 8 mL, 9 mL, or 10 mL of air or other propellant to a nostril of a subject or to a reservoir of a device. In some instances, an air source is configured to deliver between 1 least 1 mL and 10 mL, 1 mL and 8 mL, 1 mL and 5 mL, 2 mL and 10 mL, 2 mL and 8 mL, 2 mL and 7 mL, 2 mL and 6 mL, 2 mL and 5 mL, 3 mL and 10 mL or 3 mL and 8 mL of air or other propellant to a nostril of a subject or to a reservoir of a device. An air source can be configured to be activated by a force of between about 5 kPa and 100 kPa. An air source can be configured to be activated by a force of less than about 5 kPa, 6 kPa, 7 kPa, 8 kPa, 9 kPa, 10 kPa, 11 kPa, 12 kPa, 13 kPa, 14 kPa, 15 kPa, 16 kPa, 17 kPa, 18 kPa, 19 kPa, 20 kPa, 21 kPa, 22 kPa, 23 kPa, 24 kPa, 25 kPa, 26 kPa, 28 kPa, 30 kPa, 32 kPa, 33 kPa, 35 kPa, 38 kPa, 40 kPa, 42 kPa, 45 kPa, 48 kPa, or 50 kPa of pressure. An air source can be configured to provide a pressure of air or other propellant at a flow outlet of about 1 kilopascals to about 100 kilopascals, about 2 kilopascals to about 50 kilopascals, about 4 kilopascals to about 40 kilopascals, about 5 kilopascals to about 35 kilopascals; or about 10 to about 30 kilopascals.

An air source can comprise a flow inlet for filling of an air source with air or other propellant. In some embodiments, a flow inlet is in communication with an air source and with an outside environment. A flow inlet can further comprise a valve or other means for regulating the flow of air through a flow inlet. In some embodiments, a flow inlet can be configured to provide a unidirectional flow of air from the outside of an air source towards the inside of an air source. In some embodiments, a flow inlet is configured to provide for a movement from a compressed form of an air source provided by application of a compressive force and a non-compressed form of an air source provided by release of the compressive force. For example, application of compressive force by manual squeezing of an air source can provide for movement of air from an air source through a flow outlet and ultimately out of a nozzle; while, releasing of compressive force provides for movement of air into an air source via a flow inlet which in part or in whole provides for a return of an air source to a non-compressed state.

A flow inlet can be any of a number of shapes including but not limited to a cone, a cylinder, tapered cylinder, a frustum, and a parallelepiped or any other shape provided herein, including a combination of one or more of the shapes provided herein. In some embodiments, the width or diameter of a flow inlet is correlated to the width or diameter of a flow outlet. For example, the width or diameter of a flow inlet can be configured to be less than 1%, 2%, 2%, 4%, 5%, 6%, 8%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, or 90% of the width or diameter of a flow outlet. In some case, the size of a flow inlet is correlated to the size of a flow outlet. For example, the size of a flow inlet can be configured to be less than 1%, 2%, 2%, 4%, 5%, 6%, 8%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, or 90% of the size of a flow outlet.

The devices disclosed herein can be utilized for the delivery of any composition which can be delivered intranasally. Typically, the devices are used for dry powder formulations of a pharmaceutical, a neutraceutical or other desired compound. Although the disclosure below focuses on the delivery of granisetron, one of skill in the art will recognize that other pharmaceuticals can be utilized in the devices disclosed herein and the description of use with granisetron below is illustrative.

II. Compositions

A device described herein is suitable for delivering therapeutic agents including, but not limited to, free-base and salt forms of the agents. A therapeutic agent can be in crystalline or amorphous forms. A powdery therapeutic formulation can consist of just the therapeutic agent "carrier free" or they can further comprise a suitable carrier, filler, diluent, excipient, permeation enhancers, solubilizers and adjuvants or other material.

A device described herein can protect the therapeutic formulation from moisture or air until a device is prepared for use. A device can be prepared for use by removing or breaking off of a protective cover. Anhydrous compositions can be provided in a reservoir and a device can further be packaged using materials known to prevent exposure to humidity or water such that they can be included in suitable formulary kits. Examples of suitable packaging include, but are not limited to, hermetically sealed foils, plastic or the like, unit dose containers, blister packs, and strip packs.

Granisetron

Granisetron (endo-N-(9-methyl-9-azabicyclo[3.3.1]non-3-yl)-1-methyl-1H-indazole-3-carboxamide) or a pharmaceutically acceptable salt or ester thereof, can be administered intranasally for the prevention or control of emesis. Suitable pharmaceutically acceptable salts of granisetron include acid addition salts formed with organic or inorganic acids for example, hydrochlorides, hydrobromides, sulphates, phosphates, citrates, fumarates and maleates. A solvates can, for example, be hydrates. A useful form of granisetron is a hydrochloride form.

Described herein provides for the use of granisetron or a pharmaceutically acceptable salt or ester thereof in the manufacture of a medicament in the form of a dry powder for intranasal administration for the prophylaxis and/or treatment of nausea and vomiting.

Provided further herein are methods of prophylaxis and/or treatment of nausea and vomiting comprising administering to a human or animal subject, granisetron or a pharmaceutically acceptable salt or ester thereof in a dry powder formulation.

Provided herein are formulations and methods useful in the treatment of emesis, i.e., nausea, retching and vomiting. Emesis includes, but is not limited to, acute emesis, delayed emesis and anticipatory emesis. Formulations and methods provided herein are useful in the treatment of emesis however induced. For example, emesis can be induced by drugs such as cancer chemotherapeutic agents. Described herein are intranasal granisetron formulations to prevent or treat emesis induced by alkylating agents, cytotoxic antibiotics, anti-metabolites, vinca alkaloids and platinum containing compounds. Exemplary chemotherapy drugs in which an intranasal formulation will prevent or control emesis include emetogenic chemotherapy such as carmustine, cisplatin, cyclophosphamide, dacarbazine, mechlorethamine, streptozocin, carboplatin, cytarabine, doxorubicin, methotrexate, procarbazine, epirubicin, hexamethylmelamine, idarubicin, ifosfamide, irinotecan, mitoxantrone, capecitabine, docetaxel, etoposide, 5-fluorouracil, gemcitabine, mitomycin-C, paclitaxel, topotecan, bleomycin, busulfan, chlorambucil, cytarabine, 2-chlorodeoxyadenosine, fludarabine, hydroxyurea, dactnomycin, lomustine, 1-phenylalanine mustard, thioguanine, vinblastine, vincristine, vinorelbine.

Additionally, emesis can be induced with radiation therapy, e.g. irradiation of the thorax or abdomen, such as in the treatment of cancer; with the ingestion of poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness, particularly emesis from anesthetics; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Granisetron Formulations and Methods of Manufacture

General information useful for formulations described herein can be found in PCT/JP2007/074787, which is incorporated herein in its entirety. In some embodiments, a formulation for the prophylaxis or treatment of emesis and suitable for intranasal administration is prepared with granisetron comprising (a) about 1% to about 40% of granisetron, measured as the freebase; (b) about 50% to about 90% of a first crystalline cellulose with a mean particle diameter of 30 μm or less; (c) about 5% to about 15% of second crystalline cellulose with a mean particle diameter of 100 μm or less; and (d) about 0.1% to about 5% of a fluidizing agent. In further embodiments, a fluidizing agent is tribasic calcium. In further embodiments, a formulation comprises no more than about 2%, 4%, 8%, 16% or 32% granisetron, when measured as a freebase. In other embodiments, a formulation comprises about 2%, 4%, 8%, 16% or 32% granisetron, when measured as a freebase.

The first crystalline cellulose of an intranasal granisetron formulation can be Ceolus® PH-F20JP (Asahi Kasei Chemicals Corporation, Japan) or another crystalline cellulose with an equivalent particle size distribution, such as Avicel® PH-105 (FMC Corporation, US). In some embodiments, a formulation comprises about 55% to about 90% of the first crystalline cellulose. In other embodiments, the first crystalline cellulose comprises about 80% to about 90% of a formulation. In further embodiments, the first crystalline cellulose is present in no more than about 55%, 60%, 65%, 70%, 75%, 80%, 85%, or 90%. In other embodiments, a formulation comprises about 57.2%, 73.1%, 80.28%, 81.04%, 84.72%, or 86.96% of the first crystalline cellulose.

The second crystalline cellulose of an intranasal granisetron formulation can be Ceolus® PH-301 (Asahi Kasei Chemicals Corporation, Japan) or another crystalline cellulose with an equivalent particle size distribution, such as Ceolus® PH-101, PH-102, PH-301, or PH-302. In some embodiments, a formulation comprises about 5% to about 15% of the second crystalline cellulose. In other embodiments, the second crystalline cellulose comprises about 6% to about 10% of a formulation. In further embodiments, the second crystalline cellulose is present in no more than about 5%, 6%, 7%, 8%, 9%, 10%, 11%, or 12%. In other embodiments, a formulation comprises about 6.42%, 8.22%, 9.10%, or 10.00% of the second crystalline cellulose.

In some embodiments, a tribasic calcium phosphate comprises about 0.50% to about 5% of an intranasal granisetron formulation. In other embodiments, a tribasic calcium phosphate comprises no more than 0.50%, 0.80%, 0.90%, 1.00%, 1.20%, 1.40%, 1.60%, 1.80%, 2.00%, 2.20%, 2.40%, 2.60%, 2.80%, 3.00%, 4.00%, or 5.00%. In further embodiments, a tribasic calcium phosphate comprises about 0.64%, 0.80%, 0.82%, or 0.92% of a total formulation.

In some embodiments, the total weight of a formulation when dispensed in unit dosages is about 10 mg to about 200 mg per unit dosage. In further embodiments, the total weight of a formulation in a unit dosage is about 10 mg, 15 mg, 20 mg, 25 mg, 30 mg, 40 mg, 50 mg, 60 mg, 70 mg, 80 mg, 90 mg, 100 mg, 125 mg, 150 mg, 175 mg or 200 mg. In other embodiments, the total weight of a formulation in a unit dosage is no more than about 10 mg, 15 mg, 20 mg, 25 mg, 30 mg, 40 mg, 50 mg, 60 mg, 70 mg, 80 mg, 90 mg, 100 mg, 125 mg, 150 mg, 175 mg or 200 mg.

In some embodiments, a unit dosage of a granisetron formulation for the prophylaxis or treatment of emesis and suitable for intranasal administration comprising (a) about 0.5 mg to about 30 mg of granisetron, measured as the freebase; (b) a first crystalline cellulose with a mean particle diameter of 30 μm or less; (c) a second crystalline cellulose with a mean particle diameter of 100 μm or less; and (d) a fluidizing agent. In further embodiments, a fluidizing agent is tribasic calcium. In further embodiments, a unit dosage comprises no more than about 0.5 mg, 1 mg, 2 mg, 3 mg, 4 mg, 6 mg, 8 mg, 10 mg, 12 mg, 14 mg, 16 mg, 18 mg, 20 mg, 22 mg, 24 mg, 26 mg, 28 mg, or 30 mg of granisetron, when measured as a freebase. In other embodiments, a unit dosage comprises about 0.5 mg, 1 mg, 2 mg, 4 mg, 8 mg, or 16 mg of granisetron, when measured as the freebase.

In some embodiments, the first crystalline cellulose of a unit dosage of an intranasal granisetron formulation is Ceolus® PH-F20JP or another crystalline cellulose with an equivalent particle size distribution. In some embodiments, a unit dosage comprises about 15 mg to about 45 mg of the first crystalline cellulose. In other embodiments, the first crystalline cellulose comprises about 20 mg to about 41 mg of a unit dosage. In further embodiments, no more than about 20 mg, 22 mg, 24 mg, 26 mg, 28 mg, 30 mg, 32 mg, 34 mg, 36 mg, 38 mg, 40 mg, 42 mg or 44 mg of the first crystalline cellulose is present in a single dosage. In other embodiments, a unit dosage comprises about 20.07 mg, 21.18 mg, 21.74 mg, 28.60 mg, 36.55 mg, or 40.52 mg of the first crystalline cellulose.

In other embodiments, the second crystalline cellulose of a unit dosage of an intranasal granisetron formulation is Ceolus® PH-301 or another crystalline cellulose with an equivalent particle size distribution. In some embodiments, a unit dosage comprises about 1 mg to about 10 mg of the second crystalline cellulose. In other embodiments, the second crystalline cellulose comprises about 2 mg to about 5 mg of a unit dosage. In further embodiments, no more than about 1 mg, 2 mg, 3 mg, 4 mg, 5 mg, 6 mg, 7 mg, 8 mg, 9 mg or 10 mg of the second crystalline cellulose is present in a single dosage. In other embodiments, a unit dosage comprises about 2.50 mg, 3.21 mg, 4.11 mg or 4.55 mg of the second crystalline cellulose.

In some embodiments, a unit dosage of an intranasal granisetron formulation comprises about 0.10 mg to 2.00 mg of a tribasic calcium phosphate. In other embodiments, a unit dosage comprises no more than 0.10 mg, 0.20 mg, 0.30 mg, 0.40 mg, 0.50 mg, 0.60 mg, 0.80 mg, 1.00 mg, 1.20 mg, 1.40 mg, 1.60 mg, 1.80 mg or 2.00 mg of a tribasic calcium phosphate. In further embodiments, a unit dosage comprises about 0.20 mg, 0.32 mg, 0.41 mg, or 0.46 mg of a tribasic calcium phosphate.

A dry powder granisetron formulation can be manufactured numerous ways through conventional means to achieve a homogeneous mixture. For instance, using a mortar and pestle, V-blender, or a high shear mixer/stirrer. One example of a manufacturing process is mixing together: (i) granisetron; (ii) a first crystalline cellulose with a mean particle diameter of 60 μm or less; (iii) a second crystalline cellulose with a mean particle diameter of 100 μm or less; and (iv) a fluidizing agent. In further embodiments, a fluidizing agent is tribasic calcium. In some embodiments, granisetron is sieved prior to mixing. In further embodiments, the sieve has openings of about or less than 500 μm, 425 μm, 355 μm, 300 μm, 250 μm, 212 μm, 180 μm, 150 μm, 125 μm, 106 μm or 90 μm. In some embodiments, a tribasic calcium phosphate is sieved prior to mixing. In further embodiments, the sieve has openings of about or less than 500 μm, 425 μm, 355 μm, 300 μm, 250 μm, 212 μm, 180 μm, 150 μm, 125 μm, 106 μm, 90 μm, or 53 μm. In further embodiments, any two components are mixed together before mixing with the remaining components. In other embodiments, two mixed components are shaken before mixing with the remaining components. In further embodiments, two mixed components are sieved before mixing with the remaining components. In some embodiments, the sieve has opening of about or less than 1.4 mm, 1.118 mm, 1.00 mm, 850 μm, 710 μm, 600 μm, 500 μm, 355 μm, 300 μm or 250 μm.

Granisetron Unit Dosages

Formulations of an intranasal granisetron can be packaged or dispensed into unit dosages. In some embodiments, unit dosages are about 5 mg to about 200 mg in weight. In other embodiments, unit dosages are not more than about 5 mg, 10 mg, 15 mg, 20 mg, 25 mg, 30 mg, 35 mg, 40 mg, 50 mg, 60 mg, 70 mg, 80 mg, 90 mg, 100 mg, 125 mg, 150 mg, 175 mg or 200 mg. In some embodiments, unit dosages comprise no more than about 0.5 mg, 1.0 mg, 2.0 mg, 4.0 mg, 8.0 mg or 16 mg of granisetron. In further embodiments, 90% or less of particles are less than 300 μm in diameter, 150 μm in diameter, 100 μm in diameter, or 65 μm in diameter.

Unit dosages can be packaged in a capsule. In some embodiments, the capsules are size 1, 2, 3, or 4 capsules. In some embodiments, the capsules are hydroxypropyl methylcellulose capsules.

Granisetron Pharmacokinetics

Granisetron can be administered as an inhalable dry powder pharmaceutical formulation. A formulations have sufficient granisetron to achieve in a patient, a $C_{max}$ of at least 1, 2, 3, 4, 5, 6, 7, 8, 9, 10, 11, 12, 13, 14, 15, 16, 17, 18, 19, 20, 25, 30, 40, 50, 60, 70, 80, 90 or 100 ng/mL. In some embodiments, an inhalable dry powder formulation is administered in an amount sufficient to achieve a $C_{max}$ of at least 4 ng/mL, 12 ng/mL or 24 ng/mL. In some embodiments, an inhalable dry powder granisetron formulation achieves a blood plasma concentration in a patient of at least 5 ng/mL, 10 ng/mL, 15 ng/mL, 20 ng/mL, 25 ng/mL, 30 ng/mL, 35 ng/mL, or 40 ng/mL for at least 1, 2, 4, 6, 8, 10, or 12 hours.

In some embodiments, an inhalable dry powder formulations have a $T_{max}$ of less than 1.4 h, 1.3 h, 1.2 h, 1.1 h, 1.0 h, 0.9 h, 0.8 h, 0.7 h, 0.6 h, 0.5 h, 0.4 h, 0.3 h or 0.2 h. In some embodiments, granisetron inhalable dry powder formulations have a $T_{1/2}$ of more than 4 h, 5 h, 6 h, 7 h, 8 h, 9 h, or 10 h. In other embodiments, granisetron inhalable dry powder formulations have a $T_{1/2}$ in the range of 6 to 12 hour or 8 to 10 hours. In some embodiments, a formulations have a $AUC_{0\text{-}last}$ of at least 30 ng·h/mL, 40 ng·h/mL, 50 ng·h/mL, 60 ng·h/mL, 70 ng·h/mL, 80 ng·h/mL, 90 ng·h/mL, 100 ng·h/mL, 110 ng·h/mL, 120 ng·h/mL, 140 ng·h/mL, 160 ng·h/mL, 180 ng·h/mL, 200 ng·h/mL, 220 ng·h/mL or 240 ng·h/mL. In some embodiments, a formulations have a $AUC_{inf}$ of at least 30 ng·h/mL, 40 ng·h/mL, 50 ng·h/mL, 60 ng·h/mL, 70 ng·h/mL, 80 ng·h/mL, 90 ng·h/mL, 100 ng·h/mL, 110 ng·h/mL, 120 ng·h/mL, 140 ng·h/mL, 160 ng·h/mL, 180 ng·h/mL, 200 ng·h/mL, 220 ng·h/mL or 240 ng·h/mL. In some embodiments, granisetron formulations have an absolute bioavailability of at least 60%, 70%, 80%, 90%, 95% or 99%.

In some embodiments, granisetron inhalable dry powder pharmaceutical formulations have following 0.5 a mg dose to a human, a $C_{max}$ that is greater than about 1.0 ng/mL, greater than about 2.0 ng/mL, greater than about 3.0 ng/mL, greater than about 4.0 ng/mL, or greater than about 5.0 ng/mL. In some embodiments, granisetron inhalable dry powder pharmaceutical formulations have following a 1.0 mg dose to a human, a $C_{max}$ that is greater than about 6.0 ng/mL, greater than about 8.0 ng/mL, greater than about 10 ng/mL, greater than about 12 ng/mL, or greater than about 13 ng/mL. In some embodiments, granisetron inhalable dry powder pharmaceutical formulations have following 2.0 a mg dose to a human, a $C_{max}$ that is greater than about 10 ng/mL, greater than about 15 ng/mL, greater than about 20 ng/mL, greater than about 22 ng/mL, greater than about 24 ng/mL, greater than about 26 ng/mL, greater than about 28 ng/mL, or greater than about 30 ng/mL.

In some embodiments, granisetron is administered as an inhalable dry powder pharmaceutical formulation in an amount within the range from about 1 μg/kg to about 100 μg/kg, from about 5 μg/kg to about 50 μg/kg or from about 10 μg/kg to about 50 μg/kg. Thus, in particular embodiments, using a range of 40 kg-100 kg for an adult, the total amount of granisetron administered to a patient as a single or multiple doses will range between approximately 0.040 mg-10 mg, 0.2-5 mg, or 0.4-10 mg. In one embodiment, approximately 0.5 mg is administered to a patient. In other embodiments, approximately, 0.75 mg, 1.0 mg, 1.25 mg, 1.5 mg, 1.75 mg, 2.0 mg, 2.5 mg, 2.75 mg, 3.0 mg, 4 mg, 5 mg, 6 mg, 7 mg, 8 mg, 9 mg or 10 mg is administered to a patient. In further embodiments, a dose of granisetron to be administered is at least 0.1 mg, 0.25 mg, 0.5 mg, 0.75 mg, 1.0 mg, 1.25 mg, 1.5 mg, 1.75 mg, 2.0 mg, 2.25 mg, 2.50 mg, 2.75 mg, 3.0 mg, 3.5 mg, 4.0 mg, 5.0 mg, 6 mg, 7 mg, 8 mg, 9 mg or 10 mg. In other embodiments, a dose of granisetron to be administered is at less than 0.5 mg, 0.75 mg, 1.0 mg, 1.25 mg, 1.5 mg, 1.75 mg, 2.0 mg, 2.25 mg, 2.50 mg, 2.75 mg, 3.0 mg, 3.5 mg, 4.0 mg, 5.0 mg, 7 mg, 10 mg or 15 mg.

In some embodiments, a dose of inhalable dry powder granisetron formulation is sufficient to achieve control of chemotherapy-induced nausea and vomiting (CINV) in at least 50%, 60%, 65%, 70%, 75%, 80%, 85%, 90%, 95%, or 99% of cancer patients receiving highly emetogenic chemotherapy. Complete control is defined as not vomiting post granisetron and chemotherapy administration and not requiring further medication to control breakthrough emesis. Highly emetogenic drugs are defined as those drugs and dosing schedules that induce emesis in at least 50%, 60%, 70%, 80%, 90%, or 95% of patients receiving the therapy. In some embodiments, prevention or complete control is achieved for at least 4 h, 6 h, 8 h, 10 h, 12 h, 14 h, 16 h, 18 h, 20 h, 24 h, 26 h, 28 h, 30 h, 32 h, or 36 hours following administration. By achieving control of CINV, as used herein, is meant the prevention of emesis in at least 60% of patients, for example 60%, 65%, 70%, 75%, 80%, 85% 90%, 95%, or 100% of patients. Additionally, treatment with granisetron can be used in conjunction with other anti-emetic agents to control symptoms. In some instances, combinations of other agents with granisetron can result in controlling CINV in at least 80% of patients, for example 80%, 85% 90%, 95%, or 100% of patients.

In comparative pharmacokinetic testing with an injectable granisetron composition (e.g., Kytril®), a granisetron inhalable dry powder pharmaceutical formulation administered at 2.0 mg exhibits in a patient a Cmax which is greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, or greater than about 160% of the $C_{max}$ exhibited by intravenous granisetron administered at 10 μg/kg.

Following administration of a 2 mg dose of a granisetron inhalable dry powder pharmaceutical formulation to a patient, the resulting $C_{max}$ is preferably greater than about 5.0 ng/mL, greater than about 8.0 ng/mL, greater than about 10.0 ng/mL, greater than about 12.0 ng/mL, greater than about 15.0 ng/mL, greater than about 18.0 ng/mL, greater than about 20.0 ng/mL, greater than about 22.0 ng/mL, or greater than about 24.0 ng/mL.

In comparative pharmacokinetic testing with an injectable granisetron composition (e.g., Kytril®) a granisetron inhalable dry powder pharmaceutical formulation administered at 2.0 mg to a patient exhibits an $AUC_{0\text{-}last}$ which is greater than about 10%, greater than about 20%, greater than about 40%, greater than about 60%, greater than about 80%, greater than about 100%, greater than about 120%, greater than about 140%, greater than about 160%, greater than about 180%, greater than about 200%, or greater than about 220% of the $AUC_{0\text{-}last}$ exhibited by intravenous granisetron administered a 10 μg/kg.

In comparative pharmacokinetic testing with an injectable granisetron composition (e.g., Kytril®) a granisetron inhalable dry powder pharmaceutical formulation administered at 2.0 mg to a patient exhibits an $AUC_{inf}$ which is greater than about 10%, greater than about 20%, greater than about 40%, greater than about 60%, greater than about 80%, greater than about 100%, greater than about 120%, greater than about 140%, greater than about 160%, greater than about 180%, greater than about 200%, or greater than about 220% of the $AUC_{inf}$ exhibited by intravenous granisetron administered a 10 μg/kg.

In some embodiments, granisetron inhalable dry powder pharmaceutical formulations produce following a 2.0 mg dose to a human, a $C_{max}$ that is greater than about 5.0 ng/mL, greater than about 10.0 ng/mL, greater than about 15.0 ng/mL, greater than about 20.0 ng/mL, greater than about 25.0 ng/mL, greater than about 30.0 ng/mL, greater than about 35.0 ng/mL, or greater than about 40 ng/mL.

In some embodiments, granisetron inhalable dry powder pharmaceutical formulations have following a 2.0 mg dose to a human, a $T_{max}$ of less than about 90 minutes, less than about 80 minutes, less than about 60 minutes, less than about 50 minutes, less than about 40 minutes, less than about 30 minutes, or less than about 20 minutes.

In some embodiments, granisetron inhalable dry powder pharmaceutical formulations have following a 2.0 mg dose to a human, a $T_{1/2}$ of at least about 4.0 hours, at least about 5.0 hours, at least about 6.0 hours, at least about 7.0 hours, at least about 8.0 hours, at least about 9.0 hours, at least about 10.0 hours, at least about 11.0 hours, at least about 12.0 hours, at least about 13.0 hours, or at least about 14.0 hours.

In some embodiments, granisetron inhalable dry powder pharmaceutical formulations have following a 2.0 mg dose to a human, a bioavailability of at least about 60%, at least about 70%, at least about 80%, at least about 90%, at least about 95% or at least about 99%.

In some embodiments, intranasal granisetron is administered at sufficient doses so that at least 50%, 60%, 70%, 80%, 90% or 95% of the patients receiving highly emetogenic chemotherapy express satisfaction with control of emesis. In some embodiments, patients administered 0.5 mg, 1.0 mg, or 2.0 mg of intranasal granisetron prior to receiving highly emetogenic chemotherapy report at least 50%, 60%, 70%, 80%, 90% or 95% satisfaction with control of emesis. In some embodiments, intranasal granisetron is administered at sufficient doses so that at least 50%, 60%, 70%, 80%, 90% or 95% of the patients receiving highly emetogenic chemotherapy express over all (global) satisfaction with an intranasal granisetron formulation for control of emesis. In some embodiments, patients administered 0.5 mg, 1.0 mg, or 2.0 mg of intranasal granisetron prior to receiving highly emetogenic chemotherapy report at least 50%, 60%, 70%, 80%, 90% or 95% overall satisfaction with the control of nausea and vomiting.

In some embodiments, an intranasal granisetron formulation is provided whereby at least 75%, 80%, 85%, 90% or 95% of the patients do not report experiencing a bad taste in their mouth for at least 30 minutes, 4 hours or 24 hours post administration. In some embodiments, an intranasal granisetron formulation is provided whereby at least 75%, 80%, 85%, 90% or 95% of the patients do not report experiencing nasal itching for at least 30 minutes, 4 hours or 24 hours post administration. In some embodiments, an intranasal granisetron formulation is provided whereby at least 75%, 80%, 85%, 90% or 95% of the patients do not report experiencing nasal discomfort or nasal burning for at least 30 minutes, 4 hours or 24 hours post administration.

In some embodiments, an intranasal granisetron formulation is provided whereby control of breakthrough nausea and vomiting is achieved in at least 60%, 70%, 80%, 85%, 90% or 95% of patients experiencing breakthrough nausea.

Intranasal Granisetron Delivery System

A drug delivery system for administering a formulation of granisetron intranasally is provided herein. In some embodiments, the system comprises a unit dosage of granisetron as described above coupled to a nasal applicator. In some embodiments, the nasal applicator is designed for repeated use. In some embodiments, the applicator designed for repeated use is a Fit-lizer™ applicator. In other embodiments, the applicator is designed for single use. Both multiple use and single use applicators can be supplied pre-loaded with an intranasal formulation.

In some embodiments, a system comprising a unit dosage of a dry powder granisetron formulation suitable for intranasal administration and a nasal applicator delivers to a patient at least 80%, 85%, 90% or 95% of granisetron in a unit dosage. In other embodiments, a system delivers a reproducible quantity or percentage of the composition to the patient. In some embodiments, the variability in delivered dose is not more than ±1%, ±2%, ±3%, ±4%, ±5% or ±6%.

Pharmaceutical Kits

A pharmaceutical kit is provided for use of a therapeutic compositions described herein. In some embodiments, a kit comprising a unit dosage of a dry powder granisetron formulation suitable for intranasal administration and a nasal applicator or dispenser is provided. In some embodiments, a therapeutic composition is present in a therapeutic quantity. In some embodiments, kits include a carrier, package, or container that is compartmentalized to receive one or more blister packs, bottles, tubes, capsules, and the like. In certain embodiments, a pharmaceutical composition is presented in a pack or dispenser device which contains one or more unit dosage forms containing a compound provided herein. In other embodiments, a pack contains metal or plastic foil, such as a blister pack. In some embodiments, a pack contains capsules, cartridges, vials, or tubes. In other embodiments, a pack or dispenser device is accompanied by instructions for administration. In some embodiments, a dispenser is disposable or single use, while in other embodiments, a dispenser is reusable. In certain embodiments, a pharmaceutical formulation is preloaded into a device. In some embodiments, nasal applicator has a volume of not more than about 3 mL, 5 mL, 10 mL, 15 mL, 20 mL, 30 mL, 40 mL, or 50 mL.

In some embodiments, a pack or dispenser also accompanied with a notice as required by a governmental agency regulating the manufacture, use, or sale of pharmaceuticals. This notice states that a drug is approved by the agency for human or veterinary administration. Such notice, for example, is a labeling approved by the U.S. Food and Drug Administration for prescription drugs, or an approved product. Compositions containing a compound provided herein formulated in a compatible pharmaceutical carrier are also prepared, placed in an appropriate container, and labeled for treatment of an indicated condition.

The articles of manufacture provided herein can also contain an intranasal administration or dispensing device. A device can rely on the patient's inspiration to transport a formulation or pumps can be provided or built into devices to assist the aerosolization and transport of a formulation. Alternatively, a propellant can be included with or it can be stored within devices.

Such kits optionally comprise an identifying description or label for containers. In further embodiments, a label is on a container with letters, numbers or other characters forming the label and attached, molded or etched into a container itself; a label is associated with a container when it is present within a receptacle or carrier that also holds the container, e.g., as a package insert. In some embodiments, a label is used to indicate that the contents are to be used for a specific therapeutic application. In yet other embodiments, a label also indicates directions for use of the contents, such as in methods described herein. A set of instructions can also be included, generally in the form of a package insert. An informational material can contain instructions on how to dispense the pharmaceutical composition, including description of the type of patients who can be treated, the schedule (e.g., dose and frequency), and the like.

EXAMPLES

Example 1

Single Use of a Device to Deliver a Therapeutic to a Subject

A device is positioned by a user whereby a nozzle of a device is at least partially positioned within a nostril of a subject. The user compresses an air source between the thumb and forefinger with approximately 25 kPa of force. A powdered medicine therapeutic residing a reservoir disposed within a nozzle of a device is delivered into the nostril of the subject. The user visually inspects a nozzle and ascertains that a sufficient amount of the therapeutic has exited a nozzle and been delivered.

Example 2

Use of a Device to Deliver a Single Dose of a Therapeutic to a Subject

A device is positioned by a user whereby a nozzle of a device is at least partially positioned within a nostril of a subject. The user compresses an air source between the thumb and forefinger with approximately 30 kPa of force. A powdered medicine therapeutic residing a reservoir disposed within a nozzle of a device is delivered into the nostril of the subject. The user visually inspects a nozzle and ascertains that a sufficient amount of the therapeutic has not exited a nozzle and been delivered. The user repeats compression of an air source until visual inspection reveals that a sufficient amount of the therapeutic has exited a nozzle and been delivered.

Example 3

Formulation Manufacturing

Example 3a

Encapsulated TRG

Dry powder intranasal granisetron formulations (TRG) were prepared by classifying and blending ingredients comprising of granisetron HCl powder (sieved using screen with 300 μm opening), two forms of crystalline cellulose powder and tribasic calcium phosphate (TCP) powder (sieved using screen with 53 μm opening) together without any other excipients, and the finished formulations were then filled into capsule.

The specific amounts of ingredients and excipients in a capsule are, for low-dose (TRG 0.5 mg capsules), 0.5 mg granisetron free-base, 21.74 mg crystalline cellulose (Ceolus® PH-F20JP), 2.5 mg crystalline cellulose (Ceolus® PH-301) and 0.2 mg TCP, for mid-dose (TRG 1.0 mg capsules), 1.0 mg granisetron free-base, 21.18 mg crystalline cellulose (Ceolus® PH-F20JP), 2.5 mg crystalline cellulose (Ceolus® PH-301) and 0.2 mg TCP, and for high-dose (TRG 2.0 mg capsules), 2.0 mg granisetron free-base, 20.07 mg crystalline cellulose (Ceolus® PH-F20JP), 2.5 mg crystalline cellulose (Ceolus® PH-301) and 0.2 mg TCP. Two batches of each dose strength were manufactured.

Capsules were packaged into 30 cc white high-density polyethylene round bottles, which were capped by polypropylene caps with pulp liner and foil inner seal. Alternatively, the dispensed medicament can be packed as a single dose. For example, a single capsule can be sealed in a bag, pouch, bottle or jar. Alternately, several doses can be packaged together. For example, multiple capsules can be placed in a bag, pouch, bottle or jar. Alternately, the medicament can be packaged as single dosage units that are physically connected by a packaging material to other dosage units as in, for example, a blister pack.

Example 3b

Pre-Loaded TRG in Single Use Device

Dry powder intranasal granisetron formulations (TRG) were prepared by classifying and blending ingredients comprising of granisetron HCl powder (sieved using screen with 300 μm opening), two forms of crystalline cellulose powder and tribasic calcium phosphate (TCP) powder (sieved using screen with 53 μm opening) together without any other excipients, and the finished formulations were then filled into the medicine reservoir (FIG. 1, 23) of a single-use applicator described herein.

The specific amounts of ingredients and excipients in the single-use applicator described herein are 2.0 mg granisetron free-base, 20.07 mg crystalline cellulose (Ceolus® PH-F20JP), 2.5 mg crystalline cellulose (Ceolus® PH-301) and 0.2 mg TCP.

Single-use applicators loaded with TRG 2.0 mg were individually packaged into aluminum pillow packs. Alternately, several doses can be packaged together. For example, multiple doses can be placed in a bag, pouch, bottle or jar. Alternately, the medicament can be packaged as single dosage units that are physically connected by a packaging material to other dosage units as in, for example, a blister pack.

Example 4

Characterization and Stability of Powder Formulations Contained in TRG

Characterization

Figure 7:
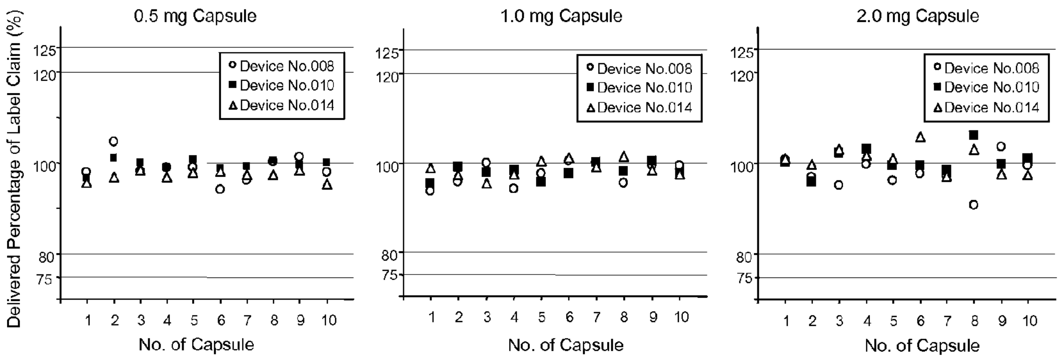
FIG. 7 illustrates uniformity of the delivered-dose from the applicator.

For powder formulation contained in TRG 0.5, 1.0 and 2.0 mg capsules prepared in Example 3a, the following characteristics were tested: appearance, identification, assay, related substance, content uniformity, water content, and microbial limits. Specifically, the results of assay testing for each batch of TRG 0.5 mg were 96.7 and 97.3%, for each batch of TRG 1.0 mg were 95.9 and 95.4%, and for each batch of TRG 2.0 mg were 97.9 and 100.9% of labeled claim. In addition to the above, the primary particle size distributions of TRG powder in capsules were examined by laser diffraction. The amount of particles less than 300 μm for each batches of TRG 0.5 mg were 100 and 100%, for each batch of TRG 1.0 mg were 100 and 100%, and for each batch of TRG 2.0 mg were 100 and 100%. The amount of particles less than 150 μm for each batches of TRG 0.5 mg were 99 and 100%, for each batch of TRG 1.0 mg were 100 and 100%, and for each batch of TRG 2.0 mg were 99 and 100%. The amount of particles less than 100 μm for each batches of TRG 0.5 mg were 97 and 100%, for each batch of TRG 1.0 mg were 97 and 99%, and for each batch of TRG 2.0 mg were 97 and 99%. The amount of particles less than 65 μm for each batches of TRG 0.5 mg were 91 and 92%, for each batch of TRG 1.0 mg were 91 and 92%, and for each batch of TRG 2.0 mg were 91 and 92%. Results are shown in FIG. 7.

For powder formulation contained in TRG 2.0 mg prepared in Example 3b, the following characteristics were tested: appearance, identification, assay, related substance, content uniformity, water content, and microbial limits Specifically, the result of assay testing was 98.3% of labeled claim. In addition to the above, the primary particle size distributions of TRG powder in were examined by laser diffraction. The amount of particles less than 300 μm was 100%, less than 150 μm was 100%, less than 100 μm was 98%, and less than 65 μm was 92%.

Stability

TRG manufactured in Example 3a have been confirmed to be stable for 1 year at room temperature (25° C., 60% relative humidity (RH)), and 6 months under accelerated conditions (40° C., 75% RH), at this point. Additionally, the primary particle size distributions of TRG manufactured in Example 3 were stable for 1 year at room temperature and 6 months under accelerated conditions, at this point. Stability at Room Temperature: All batches of TRG manufactured in Example 3a were stable for 1 year at room temperature. The assay results after 1 year for each batch of TRG 0.5 mg were 99.1 and 98.0%, for each batch of TRG 1.0 mg were 98.3 and 96.6%, and for each batch of TRG 2.0 mg were 98.3 and 98.3% of labeled claim. Additionally, there were no significant changes to the primary particle sizes after storage of 1 year at room temperature. Stability under Accelerated Conditions: All batches of TRG manufactured in Example 3a were stable (assay results of greater than 90% of label claims) for 6 months under accelerated conditions. Additionally, there were no significant changes to the primary particle sizes after storage of 6 months under accelerated conditions.

TRG manufactured in Example 3b have been confirmed to be stable for 3 months at room temperature and under accelerated conditions, at this point. Additionally, the primary particle size distributions of TRG manufactured in Example 3b were stable for 3 months at room temperature and under accelerated conditions, at this point. The assay results after 3 months at room temperature was 97.8% of labeled claim, and after 3 months under accelerated conditions was 97.3% of labeled claim. Additionally, there were no significant changes to the primary particle sizes after storage of 3 months at room temperature and under accelerated conditions.

Example 5

Delivery Devices

Example 5a

Multiple-Use Device

Figure 5:
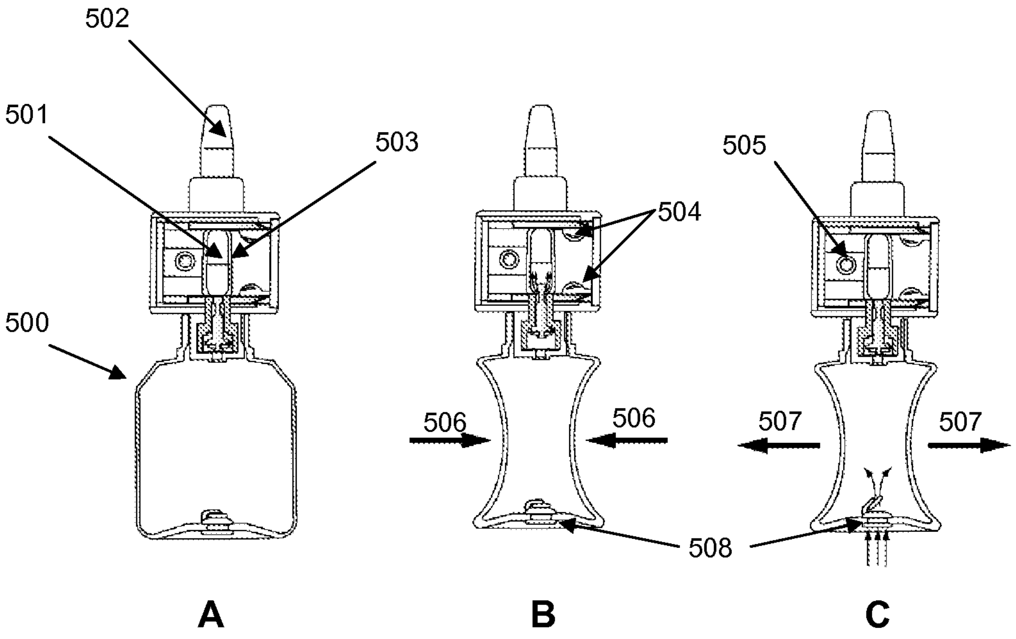
FIG. 5 illustrates actuation mechanism of an applicator. Panel A indicates the applicator in standard condition. Panel B indicates the applicator in a condition of pressure being applied to the air pump. Panel C indicates the applicator pump being released, drawing air from the bottom of the pump.

TRG is delivered into the nasal cavity using an applicator described herein. An applicator described herein, an air-driven device, is designed for intranasal delivery of TRG. As shown in FIG. 5, a TRG capsule (501) is placed inside the chamber (503) of a device and when the chamber is closed, blades slice holes in the top and bottom of the capsule, allowing the TRG to be released. Maintenance of the proper position of the capsule and other portions of the upper chamber is achieved via a locking mechanism (505). A locking mechanism (505) can comprise a ball bearing or other structure which allows for gliding of the moving parts of the device. Release of the TRG is achieved through a nozzle (502) which can be separate from the capsule. Sliced tips of the capsule are retained in receptacles (504). Once the capsule is loaded into an applicator described herein, patients can manually pump a device easily by applying inward pressure (506) on the pump, and deliver the TRG through the single nozzle of a device into the nasal cavity. Upon relaxing the pressure (507), for example by a user no longer squeezing the manual pump, the manual pump (500) is reinflated with air. Air enters through a one-way pump (508) which is closed when the device is not in use (FIG. 5, panel A), or when inward pressure is applied (FIG. 5, panel B). Additionally, airflow is prevented into the manual pump from the capsule (501) during relaxing of pressure by the closed position of the poppet. The same device can be used repeatedly, by loading another capsule. TRG is administered into the nasal cavity using an applicator described herein. The shape and secondary particle size of TRG powder emitted from an applicator described herein were analyzed to evaluate the delivery characteristics of TRG powder generated in combination with an applicator described herein. To collect data on the delivery characteristics, a mechanical auto-actuator for an applicator described herein pump, which enables the production of a pump-actuation behavior observed in human volunteers, was used.

Example 5b

Single-Use Device

TRG is delivered into the nasal cavity using an applicator described herein. An applicator described herein, an air-driven device, is designed for intranasal delivery of TRG. As shown in FIG. 1, powder formulation is pre-filled in the device. Upon use, the plastic tab or an airtight cap is removed, as shown in FIG. 4, thereby clearing the pathway of the powder formulation, allowing the TRG to be released. Once the plastic tab or an airtight cap is removed from an applicator described herein, patients can manually pump a device easily, and deliver the TRG through the single nozzle of a device into the nasal cavity. TRG is administered into the nasal cavity using an applicator described herein. The shape and secondary particle size of TRG powder emitted from an applicator described herein were analyzed to evaluate the delivery characteristics of TRG powder generated in combination with an applicator described herein. To collect data on the delivery characteristics, a mechanical auto-actuator for an applicator described herein pump, which enables the production of a pump-actuation behavior observed in human volunteers, was used.

Example 6

Delivery Characteristics

Example 6a

Delivery Characteristics of TRG in Example 3a Emitted from Device in Example 5a TRG is administered into the nasal cavity using an applicator described herein. Thus, the delivery performance of an applicator described herein plays a significant role to determine an actual dose of TRG administered in the nasal cavity. To determine the characteristics of delivery from an applicator described herein, a mechanical auto-actuator for an applicator described herein pump, which enables the production of a pump-actuation behavior observed in human volunteers, was used.

Actuation Force of a Device Pump Observed in Human Volunteers

First the hand pump-actuation parameters of an applicator described herein, stroke length, actuation velocity, and actuation acceleration were collected from volunteers using a special measurement system of the actual hand pump-actuation force. From among the observed parameters, optimal parameters which enable consistent delivery were determined: stroke length of 26.1 mm, actuation velocity of 152 mm/s, and actuation acceleration of 3385 mm/$s^2$.

Secondary Particle Size.

Secondary particle size distribution of TRG powder described in Example 3a emitted from an applicator described in Example 5a was evaluated using the laser diffraction analyzer and automatic actuation machine using the optimal pump-actuation parameters. The secondary particle size distributions measured are listed in Table 1. Furthermore, it was found that the particle size with volume under 50% measured in the secondary particle size analysis was approximately 1.5 times larger than that in the primary particle size analysis of TRG powder.

TABLE 1

Secondary Particle Size

| Parameter Particle Size (μm) | Strength TRG 0.5 mg Capsule n 4 Average ± SD | TRG 1.0 mg Capsule 4 Average ± SD | TRG 2.0 mg Capsule 4 Average ± SD |
|---|---|---|---|
| Volume under 90% | 541.7 ± 22.5 | 466.2 ± 79.0 | 543.1 ± 33.7 |
| Volume under 50% | 32.0 ± 3.4 | 28.8 ± 0.7 | 32.2 ± 3.1 |
| Volume under 10% | 9.9 ± 1.5 | 9.6 ± 0.5 | 10.0 ± 0.9 |

Effect of Pump-Actuation Velocity on Delivered Percentage of Intranasal Granisetron Powder from an applicator described herein: The effect of pump actuation velocity on the percentage emitted from an applicator described herein was evaluated by calculating the weight difference of an applicator described herein using an automatic actuator. Pump actuation parameters with the minimum and maximum velocity reproducible by automatic actuator were selected from the observed parameters in the hand pump actuation study.

As shown in Table 2, the percentages delivered from an applicator described herein when actuated 3 times were more than 90% at all of a pump actuation parameters. It was concluded that the percentage of TRG powder emitted from an applicator described herein was not affected by the force of pump actuation.

TABLE 2

Force of Pump-Actuation vs. Delivered Percentage.

| Pump-Actuation Velocity (Actuation parameters) | TRG Capsule 1.0 mg Capsule n 3 Average ± SD |
|---|---|
| Minimum (Length, 27.4 mm; Velocity, 54 mm/s; Acceleration, 898 $mm/s^2$) | 93.6% ± 2.4 |
| Optimal (Length, 26.1 mm; Velocity, 152 mm/s; Acceleration, 3385 $mm/s^2$) | 99.7% ± 1.6 |

TABLE 2-continued

Force of Pump-Actuation vs. Delivered Percentage.

| Pump-Actuation Velocity (Actuation parameters) | TRG Capsule 1.0 mg Capsule n 3 Average ± SD |
|---|---|
| Maximum (Length, 26.1 mm; Velocity, 210 mm/s; Acceleration, 3385 $mm/s^2$) | 98.9% ± 1.4 |

Plume Geometry

Plume geometry data provide information on the shape of the plume of TRG powder generated from a nozzle of an applicator described herein after pump actuation. Plume geometry measurements typically involve quantification of plume angle and plume width. Plume geometry of TRG powder emitted from an applicator described herein were evaluated at 30 mm from a nozzle tip using the analyzer with the horizontal or vertical laser sheet technology which is designed for automated plume geometry measurement, and automatic actuator using the optimal pump-actuation parameters. The data of plume geometry measured are listed in Table 3. As shown in the data for the plume geometry, the variations in the plume angle and width were low among the tested devices and among the three active doses of TRG capsule.

From the results, it was concluded that the delivery shape characteristics of TRG powder emitted from an applicator described herein were very consistent and reproducible without regard to the compositional differences of TRG capsules.

TABLE 3

Plume Geometry of TRG Powder

| Parameter Plume Geometry | Distance | Strength TRG 0.5 mg Capsule n 4 Average ± SD | TRG 1.0 mg Capsule 4 Average ± SD | TRG 2.0 mg Capsule 4 Average ± SD |
|---|---|---|---|---|
| Plume angle (°) | 30 mm | 26.1 ± 2.8 | 25.1 ± 1.0 | 26.7 ± 3.9 |
| Plume width (mm) | 30 mm | 14.0 ± 1.6 | 13.4 ± 0.6 | 14.3 ± 2.2 |

Delivered-Dose Uniformity of TRG Powder

The delivered-dose uniformity of TRG powder from an applicator described herein was evaluated. This test was designed to demonstrate the uniformity of medication per delivery, consistent with the label claim, emitted from an applicator described herein of 10 capsules. An applicator described herein was actuated 3 times per capsule using automatic actuator with the optimal actuation parameters. Three devices were allocated for each run of one active dose of TRG capsule, respectively. TRG powder emitted from an applicator described herein was trapped in the trapping bag and the amount of granisetron trapped was determined by HPLC. For samples tested in each dose, none were outside of 80 to 110% of the label claim, and the mean was not outside of 85 to 110% of label claim. The average delivered dose for TRG 0.5 mg was 98.5±2.1%, for TRG 1.0 mg was 98.1±2.1%, and for TRG 2.0 mg was 99.7±3.3%.

Example 6b

Delivery Characteristics of TRG in Example 3b Emitted from Device in Example 5b

TRG is administered into the nasal cavity using an applicator described herein. Thus, the delivery performance of an applicator described herein plays a significant role to determine an actual dose of TRG administered in the nasal cavity. To determine the delivery characteristics of an applicator described herein, a mechanical auto-actuator for an applicator described herein pump, which enables the production of a pump-actuation behavior observed in human volunteers, was used.

Actuation Force of a Device Pump Observed in Human Volunteers

First the hand pump-actuation parameters of an applicator described herein, stroke length, actuation velocity, and actuation acceleration were collected from volunteers using a special measurement system of the actual hand pump-actuation force. From among the observed parameters, optimal parameters which enable consistent delivery were determined: stroke length of 8.9 mm, actuation velocity of 74 mm/s, and actuation acceleration of 1365 $mm/s^2$.

Secondary Particle Size.

Secondary particle size distribution of TRG powder described in Example 3b emitted from an applicator described in Example 5b was evaluated using the laser diffraction analyzer and automatic actuation machine using the optimal pump-actuation parameters. The secondary particle size distributions measured are listed in Table 4.

TABLE 4

Secondary Particle Size

| Parameter<br>Particle Size (μm) | Strength<br>TRG 2.0 mg in<br>single-use device<br>n<br>10<br>Average ± SD |
|---|---|
| Volume under 90% | 639.8 ± 50.5 |
| Volume under 50% | 129.4 ± 114.5 |
| Volume under 10% | 14.9 ± 11.5 |

Effect of Pump-Actuation Velocity on Delivered Percentage of Intranasal Granisetron Powder from an applicator described herein: The effect of pump actuation velocity on the percentage emitted from an applicator described herein was evaluated by calculating the weight difference of an applicator described herein using automatic actuator. Pump actuation parameters for the automatic actuator were selected from the observed parameters in the hand pump actuation study.

As shown in Table 5, the percentages delivered from an applicator described herein when actuated 3 times were more than 90% at all of a pump actuation parameters. It was concluded that the percentage of TRG powder emitted from an applicator described herein was not affected by the force of pump actuation.

TABLE 5

Force of Pump-Actuation vs. Delivered Percentage.

| Pump-Actuation Velocity (Actuation parameters) | TRG 2.0 mg emitted from Single-use device Average |
|---|---|
| Minimum<br>(Length, 8.9 mm; Velocity, 48 mm/s;<br>Acceleration, 1365 $mm/s^2$) | 96.5% |
| Optimal<br>(Length, 8.9 mm; Velocity, 74 mm/s;<br>Acceleration, 1365 $mm/s^2$) | 97.9% |
| Maximum<br>(Length, 8.9 mm; Velocity, 100 mm/s;<br>Acceleration, 1365 $mm/s^2$) | 96.2% |

Plume Geometry

Plume geometry data provide information on the shape of the plume of TRG powder generated from a nozzle of an applicator described herein after pump actuation. Plume geometry measurements typically involve quantification of plume angle and plume width.

Plume geometry of TRG powder emitted from an applicator described herein were evaluated at 30 mm from a nozzle tip using the analyzer with the horizontal or vertical laser sheet technology which is designed for automated plume geometry measurement, and automatic actuator using the optimal pump-actuation parameters. The data of plume geometry measured is listed in Table 6. As shown in the data for the plume geometry, the variations in the plume angle and width were low among the tested devices. From the results, it was concluded that the delivery shape characteristics of TRG powder emitted from an applicator described herein were very consistent and reproducible.

TABLE 6

Plume Geometry of TRG Powder

| Parameter<br>Plume Geometry | Distance | Strength<br>TRG 2.0 mg in<br>single-use device<br>n<br>10<br>Average ± SD |
|---|---|---|
| Plume angle (°) | 30 mm | 24.4 ± 3.9 |
| Plume width (mm) | 30 mm | 13.0 ± 2.2 |

Delivered-Dose of TRG Powder

The delivered-dose of TRG powder from an applicator described herein was evaluated. This test was designed to demonstrate the uniformity of medication per delivery, consistent with the label claim, emitted from an applicator described herein of 10 pre-filled devices. An applicator described herein was actuated 3 times per capsule using an automatic actuator with the optimal actuation parameters. TRG powder emitted from an applicator described herein was trapped in the trapping bag and the amount of granisetron trapped was determined by HPLC. For 10 samples tested, none were outside of 80 to 110% of the label claim, and the mean was not outside of 85 to 110% of label claim. The average delivered dose for TRG 2.0 mg emitted from the single-use devices was 93.7±2.8%.

Example 7

Phase 1 Clinical Study of TRG Manufactured in Example 3a With the Applicator Described in Example 5a A prospective, single-center, open-label, uncontrolled, single ascending dose Phase 1 clinical study of TRG manufactured in Example 3a with the applicator described in Example 5a was conducted to examine the safety, nasal tolerability and the dose response in AUC and $C_{max}$ of granisetron, and to calculate the absolute bioavailability and other pharmacokinetic (PK) parameters ($T_{1/2}$, $T_{max}$, etc.) of TRG after intranasal administration in healthy male volunteers. This was an open-label safety and PK study conducted at a single site in which healthy volunteers, at weekly intervals, were given the reference intravenous dose, followed by three single escalating nasal doses of TRG at weekly intervals. Subjects were enrolled to receive granisetron intravenously followed by escalating doses of TRG at weekly intervals:

Granisetron (Kytril®) 10 μg/kg given intravenously over 3 minutes

TRG 0.5 mg administered into a single nostril

TRG 1.0 mg administered into a single nostril

TRG 2.0 mg administered into a single nostril

The reference therapy was Kytril® (Roche, Lot B0022), a commercially available intravenous formulation of granisetron (1 mg/mL granisetron for injection). Subjects received one intravenous dose of Kytril® (10 μg/kg) followed by three escalating single doses of TRG. There was a 7 day washout period between each dose.

Safety was evaluated by recording the frequency and severity of treatment-emergent adverse events (TEAEs), including subjective nasal evaluation and objective nasal examinations, laboratory assessments, vital signs, physical examinations, and electrocardiograms.

Serial blood samples for PK evaluation were drawn at the following intervals: before dosing, and 5, 10, 15, 30, 45, 60, 90 minutes and 2, 3, 4, 6, 8, 12, 24 and 30 hours after dosing with granisetron for each dose level. The following PK parameters were tested: $AUC_{0\text{-}last}$ (ng·h/mL), $AUC_{inf}$ (ng·h/mL), $T_{max}$ (hours), $C_{max}$ (ng/mL), $T_{1/2}$ (hours), clearance, and volume of distribution. No efficacy variables were assessed in this safety and PK study.

Collected data were summarized in tables listing the mean, standard deviation, minimum, median, maximum, and number of subjects for continuous data, or in tables listing count and percentage for categorical data, where appropriate. All subject data were listed by subject or by parameter. All statistical analyses were performed by using the SAS® system, Version 9.1.3.

Figure 8:
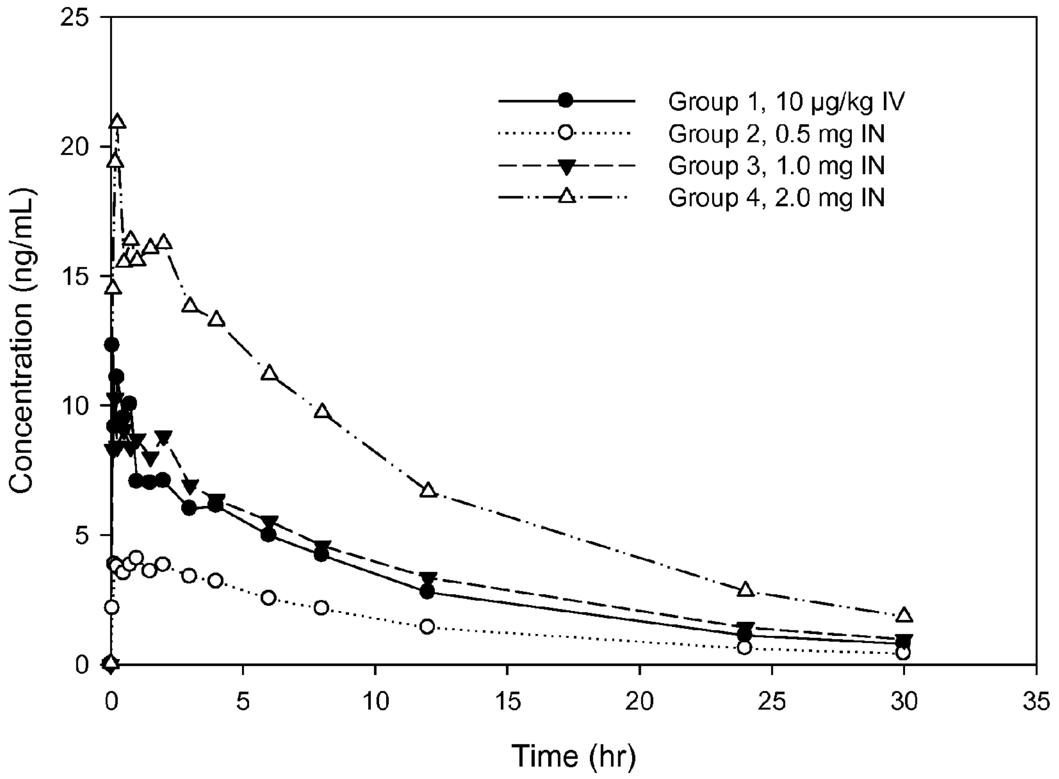
FIG. 8 illustrates the mean plasma concentration-time profiles for normal subjects receiving granisetron intravenously (10 μg/kg, Group 1) or intranasally (0.5, 1.0 and 2.0 mg, Groups 2, 3 and 4, respectively).

The PK parameters $T_{1/2}$, $T_{max}$, $C_{max}$, $AUC_{0\text{-}last}$, and $AUC_{inf}$ were calculated by using noncompartmental analysis. Values for $T_{max}$ and $C_{max}$ were reported as the observed values. Terminal elimination rate constants (λz) were determined by log-linear regression of the terminal portion of the concentration-time curves (FIG. 8). Values for $T_{1/2}$ were calculated as (ln 2)/λz, and $AUC_{0\text{-}last}$ was determined by the linear trapezoidal method. $AUC_{inf}$ was calculated as the sum of $AUC_{0\text{-}last}$ and $C_{last}$/λz where $C_{last}$ is the last measurable concentration. The absolute bioavailability (F) was calculated for each subject by the dose-corrected $AUC_{inf}$ intranasal divided by $AUC_{inf}$ intravenous. Apparent clearance and volume of distribution were also calculated. To determine the relationship between pharmacokinetic parameters ($C_{max}$, $AUC_{last}$, and $AUC_{0\text{-}\infty}$) and dosage, a multiple regression analysis was performed with log-transformed values. For other pharmacokinetic parameters, analysis of variance (ANOVA) using the mixed effect model was performed to compare between groups.

PK Results

The PK characteristics of granisetron after intravenous and intranasal administration were analyzed by noncompartmental analysis for each group in this study. Only data from the eight subjects completing the study were included in mean concentrations and in the summary statistics of the PK analysis. The concentration-time profiles are consistent with those that would be expected with intravenous and intranasal administration with first-order elimination.

Summarized PK parameter estimates for subjects receiving granisetron intravenously are listed in Table 7 below. The data show that 1.0 mg TRG has a very similar absorption profile as the 10 μg/kg intravenous dosing of granisetron.

TABLE 7

Estimated Pharmacokinetic Parameters for Subjects Receiving Granisetron Intravenously.

| Subject | Dose 10 μg/kg | | | | | | |
|---|---|---|---|---|---|---|---|
| | $T_{max}$ (h) | $C_{max}$ (ng/mL) | $T_{1/2}$ (h) | $AUC_{0\text{-}last}$ (ng · h/mL) | $AUC_{inf}$ (ng · h/mL) | CL (L/h) | Vss (L) |
| N | 8 | 8 | 8 | 8 | 8 | 8 | 8 |
| Mean | 0.18 | 16.562 | 8.52 | 92.4 | 103.0 | 9.5 | 108.4 |
| SD | 0.23 | 10.312 | 1.41 | 55.5 | 63.7 | 3.3 | 33.3 |

Definitions:
$AUC_{0\text{-}last}$ = area under the concentration-time curve from Time 0 to last measurable time point after dosing;
$AUC_{inf}$ = area under the concentration-time curve from Time 0 extrapolated to infinity;
CL = clearance;
$C_{max}$ = maximum plasma concentration;
$T_{1/2}$ = terminal elimination half-life;
$T_{max}$ = time of maximum plasma concentration;
Vss = volume of distribution steady state.

As expected after intravenous administration by rapid infusion, $T_{max}$ occurred within the first 5 to 10 minutes except for one subject. Half-life values were consistent among the members of the group with a mean of 8.52 hours. PK parameter estimates for subjects receiving 0.5, 1.0, or 2.0 mg granisetron intranasally are summarized in the Table 8 below.

TABLE 8

Estimated Pharmacokinetic Parameters for Subjects Receiving 0.5, 1.0, or 2.0 mg Granisetron Intranasally.

| Subject | $T_{max}$ (h) | $C_{max}$ (ng/mL) | $T_{1/2}$ (h) | $AUC_{0\text{-}last}$ (ng · h/mL) | $AUC_{inf}$ (ng · h/mL) | CL/F (L/h) | Vz (L) | F (%) |
|---|---|---|---|---|---|---|---|---|
| Dose = 0.5 mg | | | | | | | | |
| Mean | 1.34 | 4.953 | 8.90 | 46.9 | 52.7 | 10.6 | 131.4 | 89 |
| SD | 0.83 | 1.542 | 1.75 | 17.5 | 20.5 | 3.2 | 33.9 | 20 |

TABLE 8-continued

| Estimated Pharmacokinetic Parameters for Subjects Receiving 0.5, 1.0, or 2.0 mg Granisetron Intranasally. | | | | | | | | |
|---|---|---|---|---|---|---|---|---|
| Subject | $T_{max}$ (h) | $C_{max}$ (ng/mL) | $T_{1/2}$ (h) | $AUC_{0\text{-}last}$ (ng · h/mL) | $AUC_{inf}$ (ng · h/mL) | CL/F (L/h) | Vz (L) | F (%) |
| Dose = 1.0 mg | | | | | | | | |
| Mean | 0.34 | 13.341 | 9.52 | 105.0 | 118.6 | 9.1 | 122.6 | 107 |
| SD | 0.31 | 5.435 | 1.36 | 30.4 | 34.9 | 2.8 | 30.3 | 40 |
| Dose = 2.0 mg | | | | | | | | |
| Mean | 0.63 | 26.572 | 9.29 | 210.1 | 236.0 | 9.2 | 122.0 | 107 |
| SD | 0.85 | 8.621 | 1.73 | 59.4 | 66.2 | 3.1 | 41.7 | 41 |

Definitions:
$AUC_{0\text{-}last}$ = area under the concentration-time curve from Time 0 to last measurable time point after dosing;
$AUC_{inf}$ = area under the concentration-time curve from Time 0 extrapolated to infinity;
CL/F = apparent total body clearance;
$C_{max}$ = maximum plasma concentration;
F = absolute bioavailability;
$T_{1/2}$ = terminal elimination half-life;
$T_{max}$ = time of maximum plasma concentration;
Vz = apparent volume of distribution at elimination phase.

Although overall absorption profiles were very similar (FIG. 8), as expected, administration of intravenous granisetron was followed by a rapid T. Intranasal absorption resulted in a slightly delayed $T_{max}$; mean $T_{max}$ values for the 0.5, 1.0, and 2.0 mg doses were 1.34, 0.34, and 0.63 hours, respectively with an overall mean $T_{max}$ of 0.75 hours. The differences among the dosing groups can be due to the high PK variability of granisetron as previously reported following administration of either intravenous or oral administration. Half-life values for the 0.5, 1.0, and 2.0 mg doses were 8.90, 9.52, and 9.29 hours and proved to be fairly consistent among the subjects, routes of administration, and dose levels, with an overall mean value of 9.23 hours after intranasal administration. Absolute bioavailability was essentially 100%, with mean values for the 3 dose groups of 89%, 107%, and 107%. The 1.0 mg dose was as highly bioavailable as the intravenous dosing.

To assess dose linearity, multiple linear regression calculations of mean $C_{max}$, $AUC_{0\text{-}last}$, and $AUC_{inf}$ versus dose were done. A clear dose-linearity was found for the three doses of TRG for $C_{max}$, $AUC_{0\text{-}last}$, and $AUC_{inf}$.

In conclusion, intranasal administration is an acceptable and well absorbed route of administration of granisetron from a biopharmaceutical perspective. The bioavailability and dose linearity demonstrates this mode of administration provides an important treatment option for volunteers.

Safety Results

Eight treatment emergent adverse events (TEAEs) were reported in 6 subjects during the study. All TEAEs experienced were mild in intensity with the exception of 1 instance of headache, which was moderate in intensity and experienced by a single subject at the 1.0 mg dose. Three of these events occurred with the administration of Kytril®, and 5 occurred with the administration of any dose of TRG. TEAEs were mostly mild in nature, with 7 of 8 (87.5%) characterized as "mild" and 1 (12.5%) TEAE characterized as "moderate." Of the 7 TEAEs that were characterized as "mild", 2 (28.6%) were considered possibly related to Kytril® and 1 (14.3%) was considered possibly related to TRG by the investigator. Four mild TEAEs (57.1%) were considered unrelated to study drug. Events considered possibly related to study drug included 2 events of headache, and 1 event each of atrioventricular block first degree and prolonged corrected QT interval. Both the atrioventricular block first degree and prolonged corrected QT interval events occurred with the Kytril® and not with TRG administration. Headache was considered possibly related to TRG administration and has been previously reported for this class of drugs. The 1 TEAE (headache) that was characterized as "moderate" was experienced by Subject 102 after administration of the 1.0 mg dose of TRG. Subjects were counted once per preferred term and once per body system.

In review of all objective and subjective assessments of nasal irritation and B-SIT™, there are no significant issues at any dosage that would be considered adverse events by investigator, and no dose-response was detected. In three subjects, sneezing occurred following intranasal administration. Sneezing did not, however, affect absorption. There were no consistent changes from baseline for laboratory values, vital signs, or physical examinations.

In review of all objective and subjective assessments of nasal irritation and Brief Smell Identification Test™ (B-SIT™), there were no significant issues at any dosage that would be considered a TEAEs by the investigator, and no dose-response in TEAEs was detected. There were three instances of recorded sneezing after the administration of the intranasal formulation, and these episodes did not result in any significant change in blood levels of granisetron. There were no consistent changes from baseline for laboratory values, vital signs, or physical examinations.

Data obtained from phase 1 clinical study suggests that intranasal administration is an acceptable route of administration of granisetron from a both a biopharmaceutical and safety perspective. Intranasal administration of granisetron was well tolerated; no serious or severe adverse events were identified. Intranasal granisetron was found to have a clear dose-proportionality, and mean absolute bioavailability was approximately 100%. Intranasal granisetron provides an important alternative delivery of an anti-emesis agent to volunteers requiring chemotherapy which can induce nausea and vomiting.

Example 8

Phase 2 Clinical Study of TRG Manufactured in Example 3a With the Applicator Described in Example 5a A Phase 2 clinical study of TRG manufactured in Example 3a with the applicator described in Example 5a was conducted in female and male patients. The study was a randomized, single administration, double-blind, parallel-group phase 2 dose finding study to assess the efficacy, tolerability, and safety of TRG in patients with chemotherapy-induced nausea and vomiting (CINV) associated with the administration of highly emetogenic chemotherapy. The objective was to evaluate the safety, tolerability, dose response, efficacy, and patient satisfaction of a single dose of TRG for the prevention of acute-onset (0-24 hours) CINV. Patients received, on Day 1, a single dose of TRG 0.5 mg, 1.0 mg, or 2.0 mg, 30 to 60 minutes before the start of the first cycle of highly emetogenic chemotherapy. Patients also received dexamethasone and Emend®. Metoclopramide was made available as rescue medication. Endpoints and safety assessments are listed in Table 9.

TABLE 9

| Endpoints and Safety Assessments | |
|---|---|
| Primary Efficacy Endpoint | Proportion of patients with Complete Control, defined as no emetic episodes, no use of rescue medications, and no more than mild nausea as defined by a categorical scale, during the acute phase (0-24 hours). |
| Secondary Efficacy Endpoints | Proportion of patients with Complete Response, defined as no emetic episodes and no use of rescue medications, during the acute phase (0-24 hours).. |
| | Proportion of patients with Total Response, defined as no nausea, no emetic episodes, and no use of rescue medications, during the acute phase (0-24 hours). |
| | Proportion of patients with major control of emesis (≤2 emetic episodes), minor control of emesis (3-5 emetic episodes), and failure (>5 emetic episodes) during the acute phase (0-24 hours). |
| | Proportion of patients using rescue medication during the acute phase (0-24 hours). |
| | Time to first emetic episode during the acute phase (0-24 hours). |
| | Time to first rescue medication during the acute phase (0-24 hours). |
| | Time to treatment failure (based on time to first emetic episode or time to rescue medication, whichever occurs first) during the acute phase (0-24 hours). |
| | Number of emetic episodes during the acute phase (0-24 hours). |
| | Severity of nausea measured at selected time points during the acute phase (0-24 hours), as measured by a categorical scale. |
| | Patient global satisfaction with antiemetic therapy during the acute phase (0-24 hours), as measured by a visual analog scale (VAS). |
| Safety Assessments | Subjective assessment of nasal irritation |
| | Medical history |
| | Physical examination |
| | Vital signs |
| | Pregnancy test |
| | AEs |
| | Laboratory tests (hematology, blood chemistry, urinalysis) |

Efficacy Data

Figure 9:
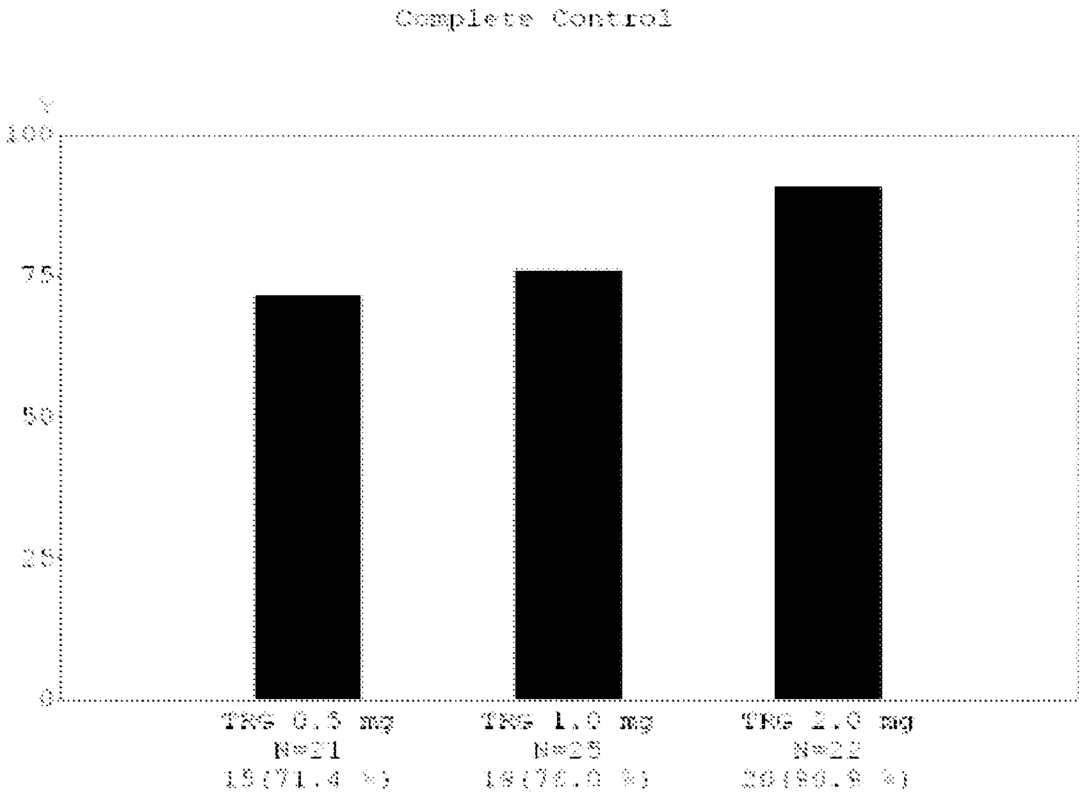
FIG. 9 illustrates the percentage of patients experiencing complete control (no emetic episodes, no use of rescue medications, and no more than mild nausea) of chemotherapy-induced nausea and vomiting (CINV) in the 24 hours post-administration of highly emetogenic cancer chemotherapy.

Complete Control (Primary Efficacy Endpoint): FIG. 9 illustrates the rate of complete control of CINV (no emetic episodes, no use of rescue medications, and no more than mild nausea) in the 24 hours post-chemotherapy. A dose response is seen with 71.4% of the patients in the TRG 0.5 mg group achieving complete control; 76.0% of the patients in the 1.0 mg group and 90.9% of the patients in 2.0 mg treatment group.

Global satisfaction assessment: In a patient global satisfaction assessment conducted 24 hours after the start of chemotherapy, the patients rated their global satisfaction with of the drug for preventing or controlling emesis with 87.7% of the patients in the 0.5 mg group, 79.8% of the patients in the 1.0 mg group and 96.6% of the patients in the 2.0 mg group expressing global satisfaction.

Safety Data: The majority of adverse events observed after the administration of TRG were deemed to be caused by chemotherapy. To assess the degree of nasal irritation caused by intranasal administration of a formulation, patients were asked to perform self assessments of nasal irritation (nasal discomfort, nasal burning, nasal itching, and bad taste) before TRG dosing, 30 minutes after TRG doing, 4 hours after dosing, and 24 hours after chemotherapy. In all treatment groups, almost no nasal irritation was observed.

While preferred embodiments have been shown and described herein, it will be obvious to those skilled in the art that such embodiments are provided by way of example only. Numerous variations, changes, and substitutions will now occur to those skilled in the art without departing from devices, methods and compositions described herein. It should be understood that various alternatives to the embodiments of described herein can be employed in practicing devices, methods and compositions described herein. It is intended that the following claims define the scope of methods, compositions and devices and that methods, compositions, and devices within the scope of these claims and their equivalents be covered thereby.

What is claimed:

1. A device comprising:

a) a nozzle having an upstream end and a downstream end adapted to allow positioning of at least a portion of the nozzle into a nostril of a subject, the nozzle having a reservoir, wherein the reservoir comprises a single dose of a powdered therapeutic formulation that is disposed within the reservoir of the nozzle;

b) a valve assembly having an upstream end and a downstream end, wherein the downstream end is coupled to the upstream end of the nozzle; and c) an air source operably linked to the upstream end of the valve assembly, wherein when the device is not in use, the reservoir is in communication with the valve assembly through an opening or a duct, and the valve assembly comprises a poppet adapted to block the movement of the powdered therapeutic formulation into the valve assembly.

2. The device of claim 1, wherein the device is adapted to deliver from about 80% to about 99% of the single dose of the powdered therapeutic formulation into the nostril of the subject.

3. The device of claim 1, wherein the device is adapted to deliver from about 80% to about 99% of the single dose of the powdered therapeutic formulation into the nostril of the subject after a single activation of the air source.

4. The device of claim 1, wherein the air source is adapted to deliver between 2 and 7 mL of air.

5. The device of claim 1, wherein the device is adapted to deliver from about 1 to about 50 mg of the powdered therapeutic formulation.

6. The device of claim 1, wherein the device is less than 50 $cm^3$ in volume.

7. The device of claim 1, wherein the device has a mass of less than 20 grams.

8. The device of claim 1, wherein the air source is adapted to be engaged by a user to force air from the air source through the valve assembly into the downstream end of the nozzle.

9. The device of claim 1, wherein the device is adapted to provide laminar airflow within at least a portion of the reservoir while the device is in use.

10. The device of claim 1, wherein the air source comprises a pump.

11. The device of claim 10, wherein the device is adapted to deliver the powdered therapeutic formulation into the nostril of the subject by application of from about 5 to about 30 kilopascals of compressive force to the pump.

12. The device of claim 10, wherein the pump further comprises a deformable volume adapted to be engaged by a user.

13. The device of claim 10, wherein the pump comprises a manual air pump.

14. The device of claim 13, wherein the manual air pump is adapted to be engaged by a user by squeezing the pump between a thumb and a forefinger, middle finger, ring finger, little finger or combination thereof.

15. The device of claim 1, wherein the reservoir comprises an inner diameter of less than 10 mm.

16. The device of claim 1, wherein the nozzle further comprises a length perpendicular to an upstream to downstream axis of between 5 mm and 20 mm.

17. The device of claim 1, wherein the nozzle further comprises a length parallel to an upstream to downstream axis of between 5 mm and 40 mm.

18. The device of claim 1, wherein the air source further comprises a flow inlet, wherein the flow inlet is less than 10% of the size of a flow outlet of the valve assembly.

19. The device of claim 18, wherein said flow inlet is between 0.1 and 2 mm in diameter.

20. The device of claim 1, wherein the nozzle further comprises an airtight cap positioned on the upstream end of the nozzle and adapted to prevent outside air from contacting the powdered therapeutic formulation.

21. The device of claim 1, wherein the nozzle further comprises a breakable cover positioned at the downstream end of the nozzle, and adapted to prevent a flow of air through the nozzle.

22. The device of claim 1, wherein the downstream end of the nozzle further comprises a flow restrictor.

23. The device of claim 22, wherein the flow restrictor further comprises a funnel shape with an upstream end and a downstream end wherein the downstream end of the flow restrictor is narrower than the upstream end.

24. The device of claim 1, wherein the valve assembly further comprises a diffuser with an upstream end and a downstream end, wherein the downstream end of the diffuser is operably linked to the upstream end of the nozzle.

25. The device of claim 24, wherein the diffuser further comprises a funnel shape with an upstream end and a downstream end wherein the upstream end of the diffuser is narrower than the downstream end of the diffuser.

26. The device of claim 1, wherein the valve assembly further comprises a throat with an upstream end and a downstream end, wherein the downstream end of the throat is operably linked to the upstream end of a diffuser.

27. The device of claim 1, wherein the valve assembly further comprises a check valve adapted to regulate a flow of air.

28. The device of claim 1, wherein the poppet is adapted to provide laminar airflow along at least a portion of the reservoir.

29. The device of claim 1, wherein at least a portion of the poppet is disposed within a throat.

30. The device of claim 1, wherein the valve assembly further comprises a check valve, and wherein the poppet comprises:

a) a downstream deflecting surface; and b) an upstream stem, wherein the deflecting surface is adapted to direct a flow of air along at least a portion of the reservoir, and a stem is operably linked to the check valve.

31. The device of claim 30, wherein the check valve comprises a valve disk adapted to move from a first position and a second position, the valve disk comprising an upstream surface adapted to regulate the flow of air from the air source through a flow outlet and into the reservoir, wherein in the first position the upstream surface is in communication with the flow outlet and thereby the flow of air into the reservoir is blocked, and in the second position the flow of air into the reservoir is allowed.

32. The device of claim 30, wherein the check valve comprises a valve disk adapted to move from a first position and a second position, the valve disk comprising:

a) an upstream surface adapted to regulate the flow of air from the air source through a flow outlet and into the reservoir, wherein in the first position the upstream surface is in communication with the flow outlet and the flow of air into the reservoir is blocked, and in the second position the flow of air into the reservoir is allowed; and b) a downstream surface operably linked to a stem of the poppet, wherein the movement of the valve disk from the first position to the second position moves the poppet from a first position to a second position, and wherein in the first position the poppet is adapted to block upstream movement of the powdered therapeutic formulation, and in the second position the poppet is adapted to direct the flow of air along at least a portion of the reservoir.

33. The device of claim 31 or 32, wherein the check valve further comprises a spring operable to maintain the valve disk in the first position absent a sufficient flow of air, and wherein the spring is operable to maintain the valve disk in the second position in the presence of the sufficient flow of air.

34. The device of claim 31, wherein a deflecting surface of the poppet in the second position is disposed within a diffuser of the valve assembly.

35. The device of claim 33, wherein the sufficient flow of air is generated by a compression force of at least 20 kilopascals applied to the air source.

36. The device of claim 1, wherein the nozzle is comprised of a substantially clear or translucent material.

37. The device of claim 1, wherein the nozzle further comprises at least one engaging ratchet adaptable to secure the nozzle to the valve assembly.

38. The device of claim 1, wherein the nozzle further comprises an engaging hole adaptable to secure the nozzle to the valve assembly.

39. The device of claim 1, wherein the valve assembly further comprises at least one engaging hole adaptable to secure the valve assembly to the nozzle.

40. The device of claim 1, wherein the valve assembly further comprises at least one engaging ratchet adaptable to secure the valve assembly to the nozzle.

41. The device of claim 1, wherein the device is a single-use device.

42. A method of using a device to deliver a powdered therapeutic formulation in a subject, wherein the method comprises positioning a nozzle of the device into the nostril of the subject and activating a manual air pump, and wherein the device is a single-use device that comprises:

a) the nozzle having an upstream end and a downstream end, the nozzle adapted to allow positioning of at least a portion of the nozzle into the nostril of the subject, wherein the nozzle has a reservoir comprising a dose of the powdered therapeutic formulation that is disposed within the nozzle;

b) a valve assembly having an upstream end and a downstream end, wherein the downstream end is coupled to the upstream end of the nozzle; and c) the manual air pump operably linked to the upstream end of the valve assembly, wherein when the device is not in use, the reservoir is in communication with the valve assembly through an opening or a duct, and the valve assembly comprises a poppet adapted to block the movement of the powdered therapeutic formulation into the valve assembly.

43. The method of claim 42, wherein the nozzle of the device comprises clear or translucent material and wherein the method further comprises visually inspecting the amount of the powdered therapeutic formulation remaining in the reservoir and repeating the method of claim 42 until a sufficient dose is delivered.

44. The method of claim 42, wherein the method further comprises activating the manual air pump to produce laminar flow along at least a portion of the reservoir.

45. The method of claim 42, wherein the method further comprises delivering from about 1 mg to about 50 mg of the powdered therapeutic formulation to the nostril of the subject.

46. The method of claim 42, wherein the method further comprises delivering from about 80% to about 99% of a single dose of the powdered therapeutic formulation to the nostril of the subject.

47. The method of claim 42, wherein the method further comprises compressing the manual air pump with from about 5 to about 30 kilopascals of force.

48. A method of manufacturing a device for delivering a powdered therapeutic formulation to a subject, wherein the method comprises providing the powdered therapeutic formulation to a reservoir of a nozzle and subsequently coupling the nozzle to a valve assembly, wherein the device comprises:

a) the nozzle having an upstream end and a downstream end, the nozzle adapted to allow positioning of at least a portion of the nozzle into a nostril of a subject, the nozzle having a reservoir, wherein the reservoir comprises a dose of the powdered therapeutic formulation that is disposed within the reservoir of the nozzle;

b) the valve assembly having an upstream end and a downstream end, wherein the downstream end is coupled to the upstream end of the nozzle; and c) a manual air pump operably linked to the upstream end of the valve assembly, wherein when the device is not in use, the reservoir is in communication with the valve assembly through an opening or a duct, and the valve assembly comprises a poppet adapted to block the movement of the powdered therapeutic formulation into the valve assembly.

* * * * *